(12) United States Patent
Weiman et al.

(10) Patent No.: US 10,874,523 B2
(45) Date of Patent: *Dec. 29, 2020

(54) ARTICULATING EXPANDABLE INTERVERTEBRAL IMPLANT

(71) Applicant: GLOBUS MEDICAL, INC., Audubon, PA (US)

(72) Inventors: Mark Weiman, Downingtown, PA (US); Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/977,294

(22) Filed: May 11, 2018

(65) Prior Publication Data
US 2018/0325693 A1    Nov. 15, 2018

Related U.S. Application Data

(63) Continuation of application No. 14/885,252, filed on Oct. 16, 2015, now Pat. No. 10,004,607, which is a continuation-in-part of application No. 13/963,720, filed on Aug. 9, 2013, now Pat. No. 9,198,772, which is a continuation-in-part of application No. 13/782,724, filed on Mar. 1, 2013, now Pat. No. 9,204,972.

(51) Int. Cl.
| A61F 2/44 | (2006.01) |
| A61F 2/30 | (2006.01) |
| A61F 2/46 | (2006.01) |

(52) U.S. Cl.
CPC ............ *A61F 2/4465* (2013.01); *A61F 2/447* (2013.01); *A61F 2/4455* (2013.01); *A61F 2002/30387* (2013.01); *A61F 2002/30507* (2013.01); *A61F 2002/30538* (2013.01); *A61F 2002/30556* (2013.01); *A61F 2002/30579* (2013.01); *A61F 2002/30772* (2013.01); *A61F 2002/30904* (2013.01); *A61F 2002/443* (2013.01); *A61F 2002/4629* (2013.01)

(58) Field of Classification Search
CPC .......... A61F 2/44; A61F 2/442; A61F 2/4425; A61F 2/4455–447; A61F 2002/443
See application file for complete search history.

(56) References Cited

U.S. PATENT DOCUMENTS

| 7,070,598 | B2 | 7/2006 | Lim et al. |
| 7,909,876 | B2 | 3/2011 | Dooris et al. |
| 8,211,178 | B2 | 7/2012 | Melkent et al. |
| 8,900,305 | B2 | 12/2014 | Stad et al. |
| 2012/0265309 | A1 * | 10/2012 | Glerum ................... A61F 2/447 623/17.16 |
| 2014/0249628 | A1 | 9/2014 | Weiman |

* cited by examiner

*Primary Examiner* — Amy R Sipp

(57) ABSTRACT

A spacer for separating bones of a joint, the spacer includes a frame having a longitudinal axis, and ramped surfaces. An endplate configured to engage a bone of the joint has ramped surfaces mateable with the ramped surfaces of the frame. When the endplate is moved relative to the frame in a direction along the longitudinal axis of the frame, the endplate is moved in a direction away from the frame to increase the height at least one end of the spacer. A second endplate configured to engage a second bone of the joint can be similarly configured.

12 Claims, 15 Drawing Sheets

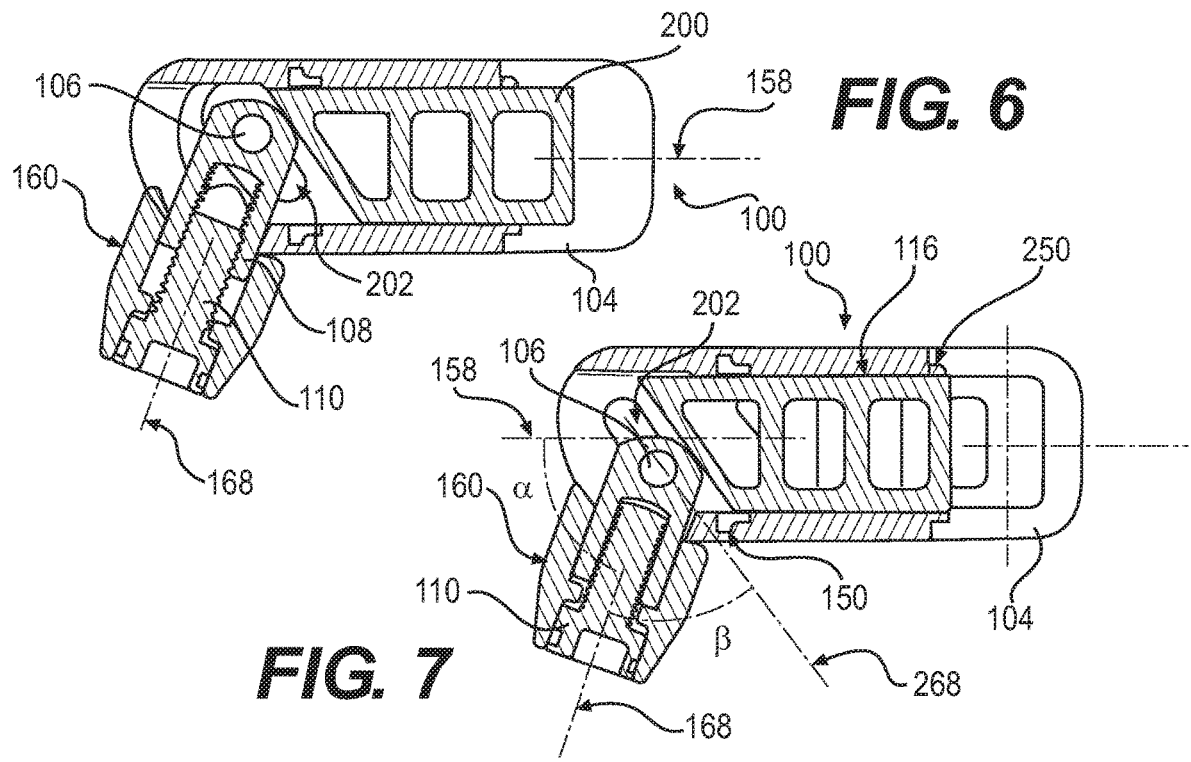
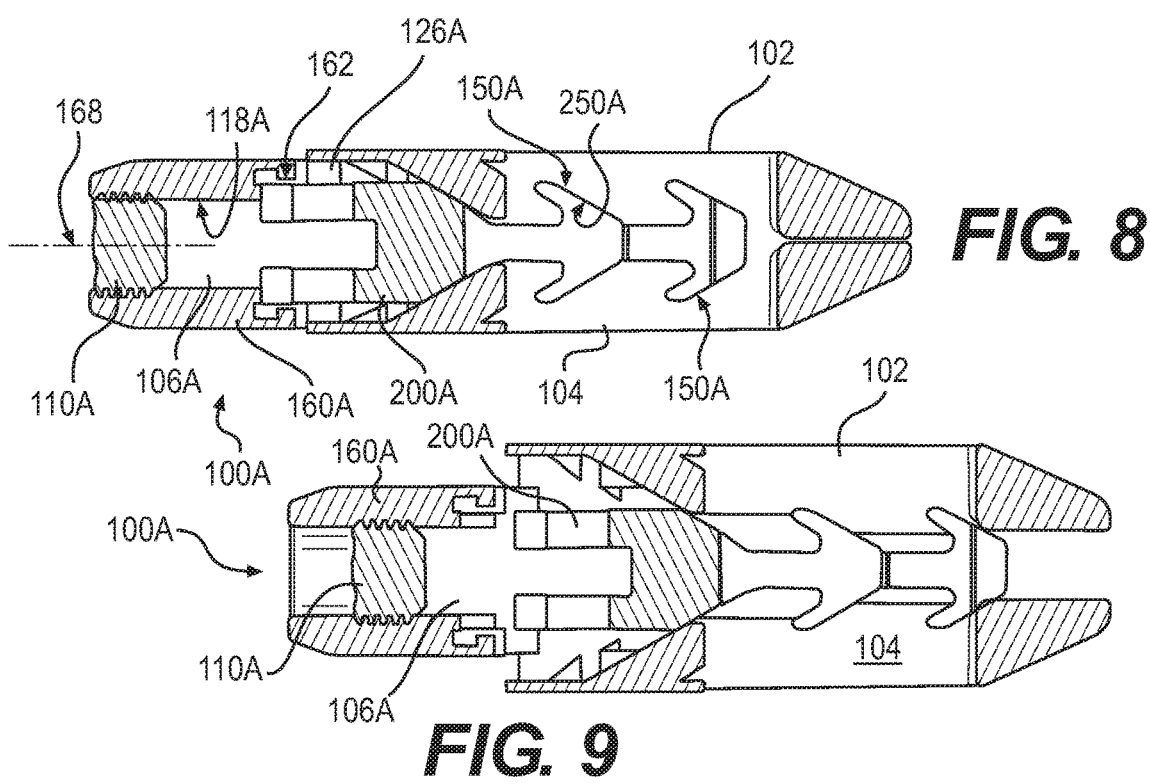

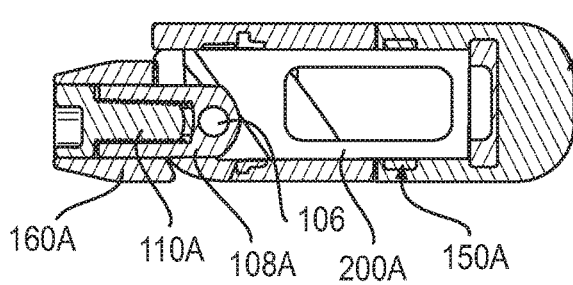
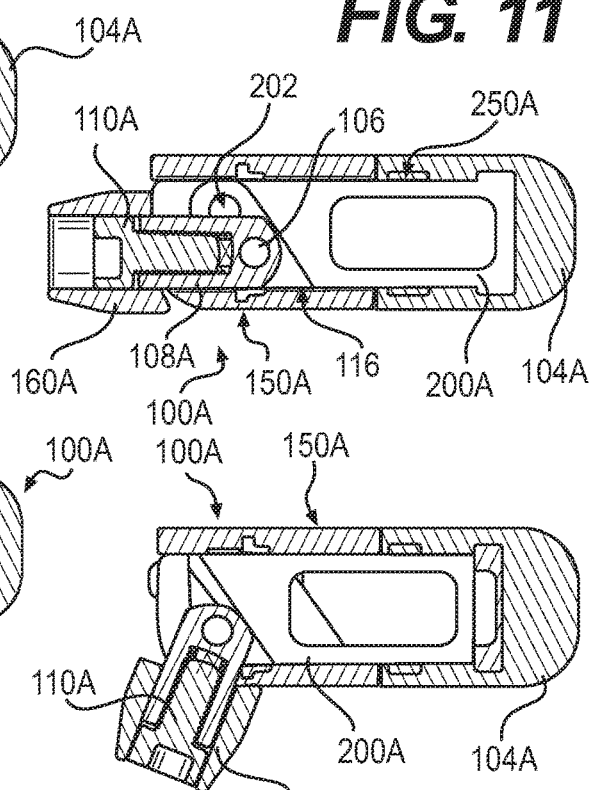
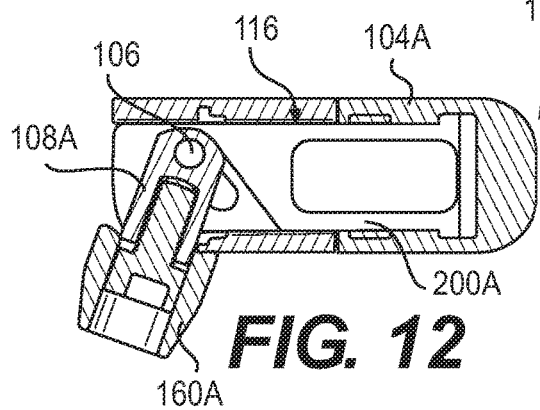
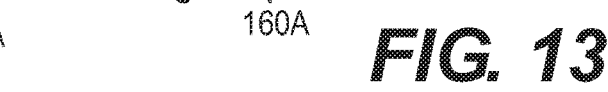
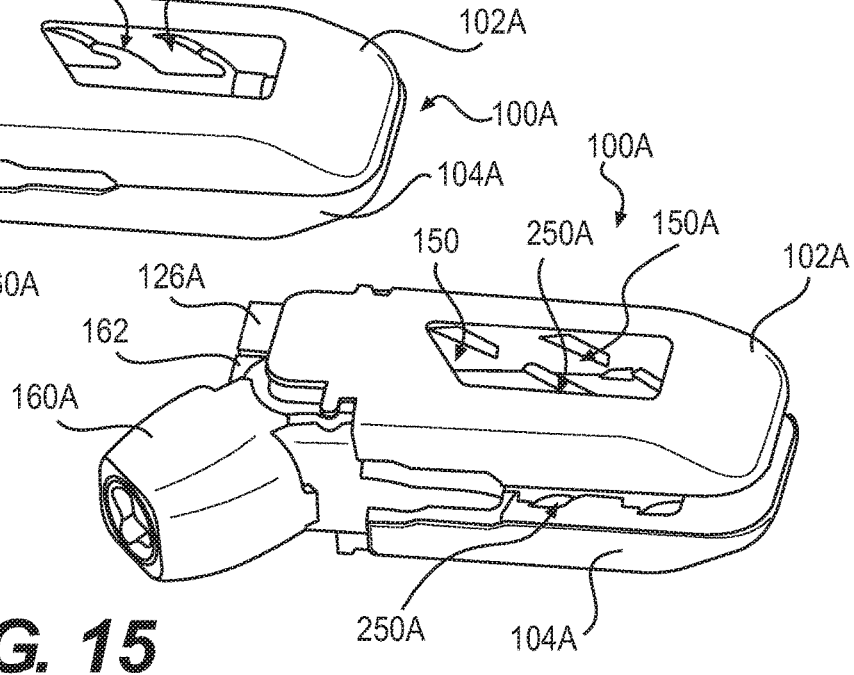

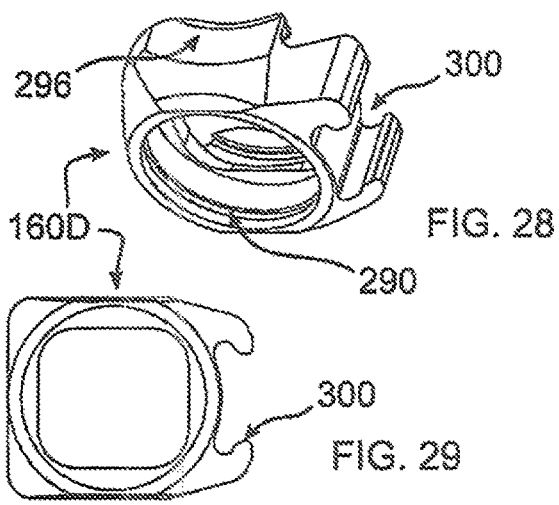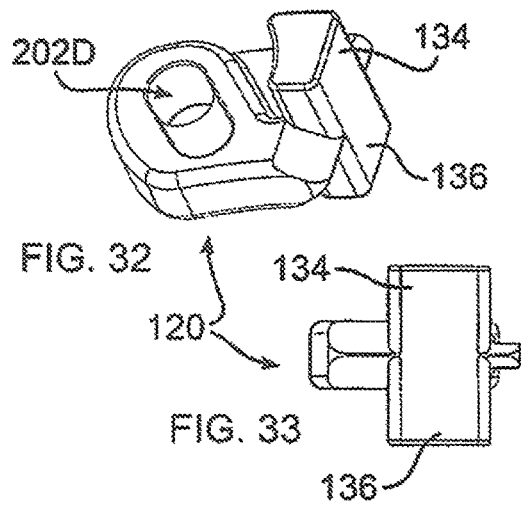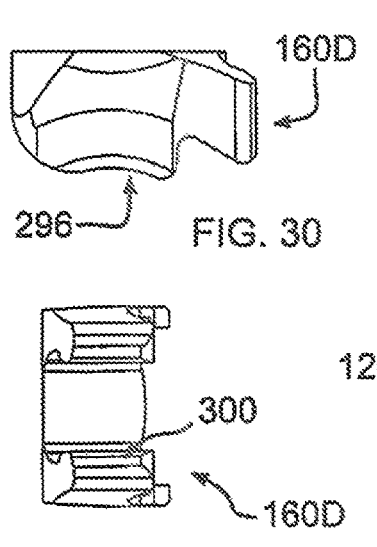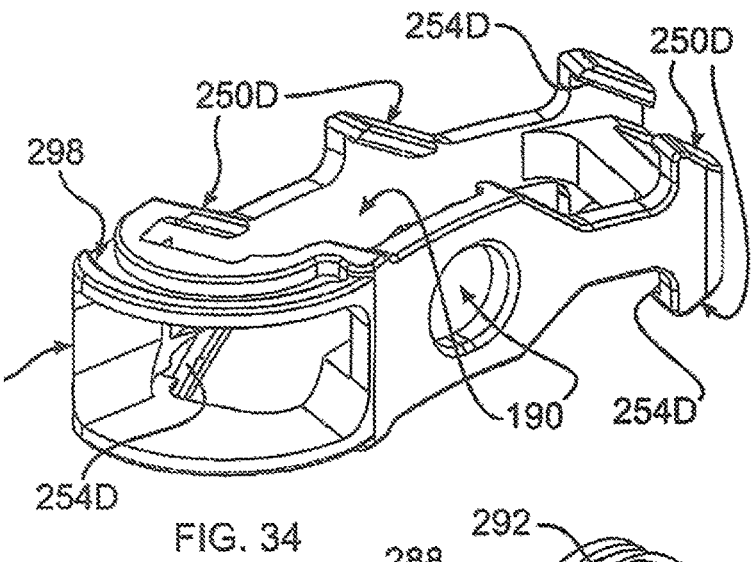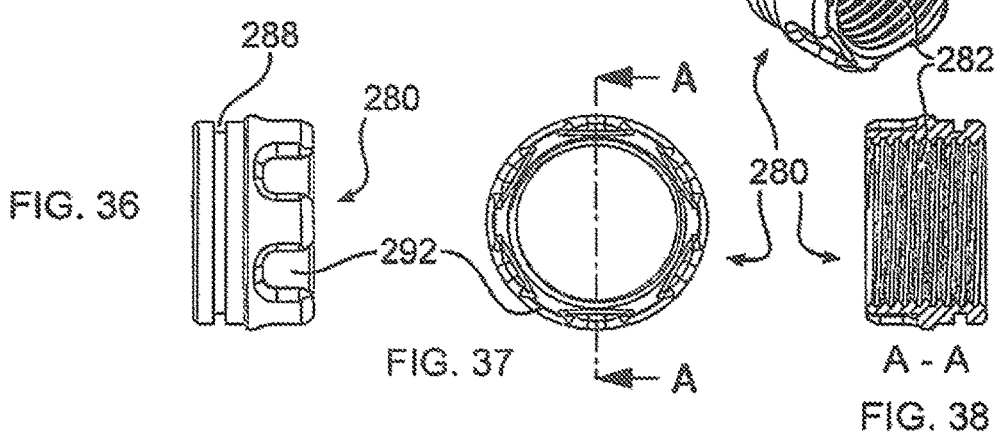

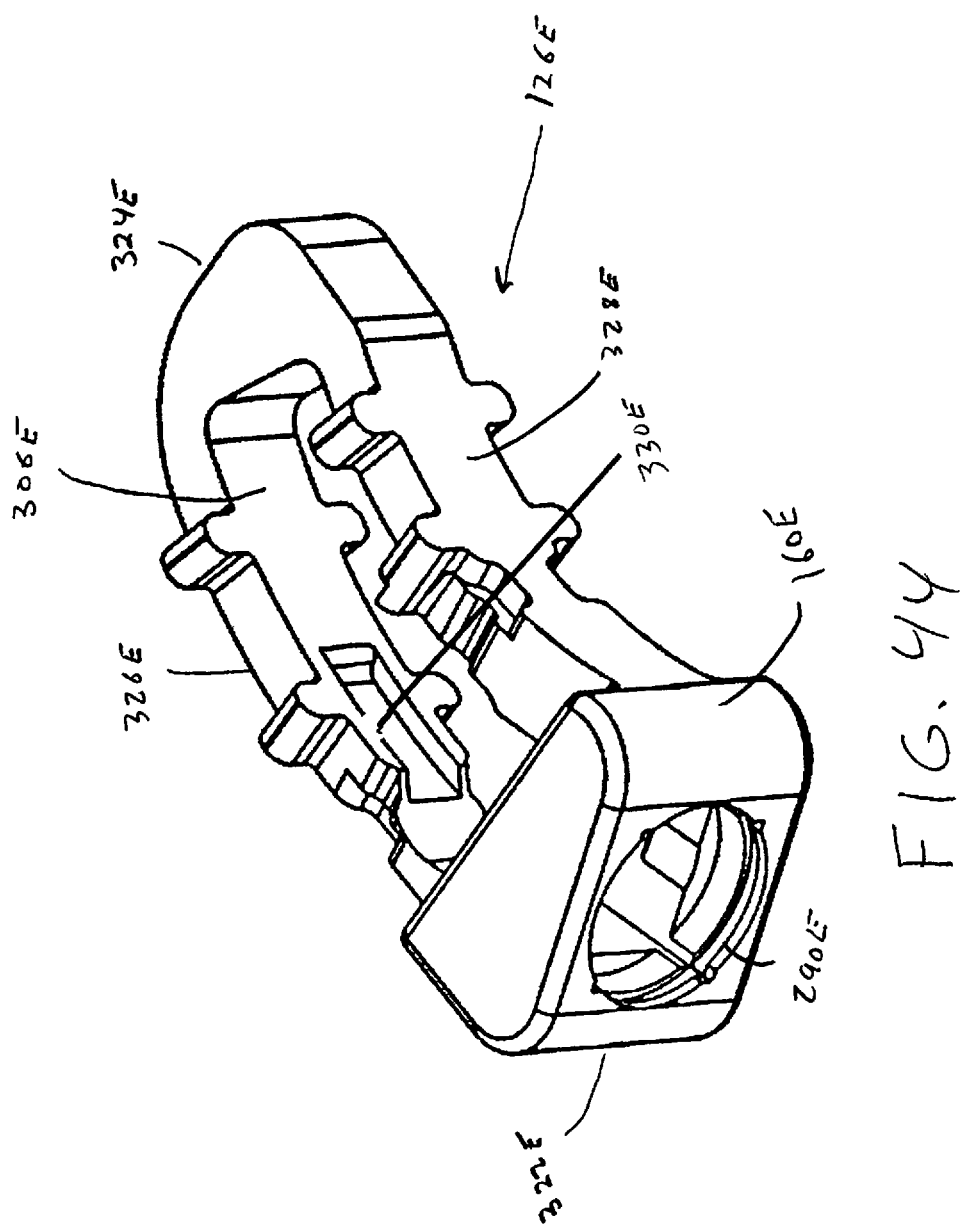

ARTICULATING EXPANDABLE INTERVERTEBRAL IMPLANT

CROSS REFERENCE TO RELATED APPLICATIONS

This application is a continuation application of U.S. patent application Ser. No. 14/885,252 filed on Oct. 16, 2015 which is a continuation-in-part application of U.S. patent application Ser. No. 13/963,720 filed on Aug. 9, 2013, which is a continuation-in-part application of U.S. patent application Ser. No. 13/782,724 filed on Mar. 1, 2013, the disclosure of which are incorporated by their entirety herein.

FIELD OF THE INVENTION

This invention relates to stabilizing adjacent vertebrae of the spine by inserting an intervertebral spacer, and more particularly an intervertebral spacer that is adjustable in height.

BACKGROUND

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY

In accordance with an embodiment of the disclosure, a spacer for separating bone of a joint may be provided. The spacer may comprise a frame having a longitudinal axis, and having at least one ramped surface. The spacer may further comprise a first endplate configured to engage a first bone of the joint. The first endplate may have at least one ramped surface mateable with the at least one ramped surface of the frame, whereby when the first endplate is moved relative to the frame in a direction along the frame longitudinal axis, at least one end of the first endplate is moved in a direction away from the frame to open the spacer. The spacer may further comprise a second endplate configured to engage a second bone of the joint. The spacer may further comprise a link moveable with respect to the frame. The link may have projection pivotally engageable with the first endplate to thereby move the first endplate along the frame longitudinal axis when the link is moved with respect to the frame. The spacer may further comprise an actuating screw moveable with respect to the frame and connected to the link to cause movement of the link when the actuating screw is moved with respect to the frame. The spacer may be inserted between bones of the joint. The actuating screw may be rotated rotating the actuating screw to cause the link to move and thereby displace the first and second endplate, wherein the at least one ramped surface of the first ramped surface slides along the at least one ramped surface of the frame to cause at least one end of the first endplate to move in a direction away from the frame while the opposite end of the first endplate pivots at the link.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which:

FIG. 6 depicts a cross section through the spacer of FIG. 1;

FIG. 7 depicts the spacer of FIG. 6, the endplates relatively separated;

FIG. 8 depicts a cross section of an alternative spacer of the disclosure shown in FIG. 14, the endplates separated by pushing a carriage, having a screw support aligned with a longitudinal axis of the spacer;

FIG. 9 depicts the spacer of FIG. 8, the endplates separated;

FIG. 10 depicts the spacer of FIG. 8, taken along an orientation 90 degrees offset from the orientation of the spacer of FIG. 8;

FIG. 11 depicts the spacer of FIG. 10, the endplates separated;

FIG. 12 depicts the spacer of FIG. 11, the screw support disposed at an angle with respect to the frame;

FIG. 13 depicts the spacer of FIG. 10, the screw support disposed at an angle with respect to the frame;

FIG. 14 is a perspective view of an alternative embodiment of a spacer of the disclosure, including a carriage which is pushed to separate endplates, and an actuator screw which is displaced within a screw support;

FIG. 15 depicts the spacer of FIG. 14, the endplates separated;

FIGS. 28-31 are alternative views of the actuating screw support of the spacer of FIG. 22;

FIGS. 32-33 are alternative views of the drive link of the spacer of FIG. 22;

FIG. 34 is a perspective view of the frame of the spacer of FIG. 22;

FIGS. 35-38 are alternative views of the nut of the spacer of FIG. 22;

FIG. 44 illustrates the frame of the spacer of FIG. 39;

FIG. 49 is a cutaway view illustrating the spacer of FIG. 39 in a collapsed configuration with an endplate removed; and FIG. 50 is a cutaway view illustrating the spacer of FIG. 39 in an open configuration with an endplate removed.

DETAILED DESCRIPTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
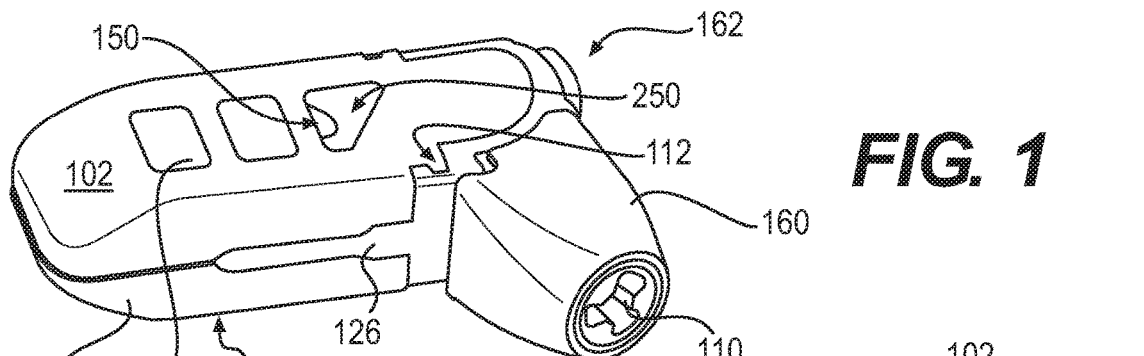
FIG. 1 is a perspective view of a spacer implant of the disclosure, with an articulating screw support.
Figure 2:
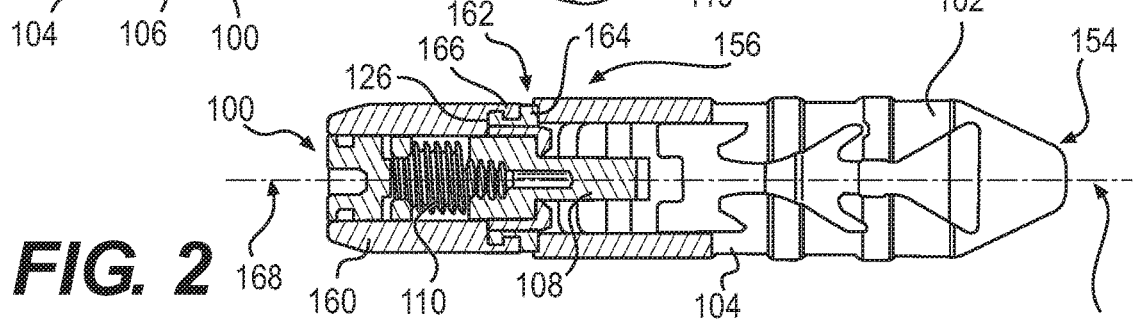
FIG. 2 depicts a cross section of the spacer of FIG. 1, taken through an actuating screw of the spacer, with the screw support oriented longitudinally, as further illustrated in FIGS. 4 and 5.
Figure 3:
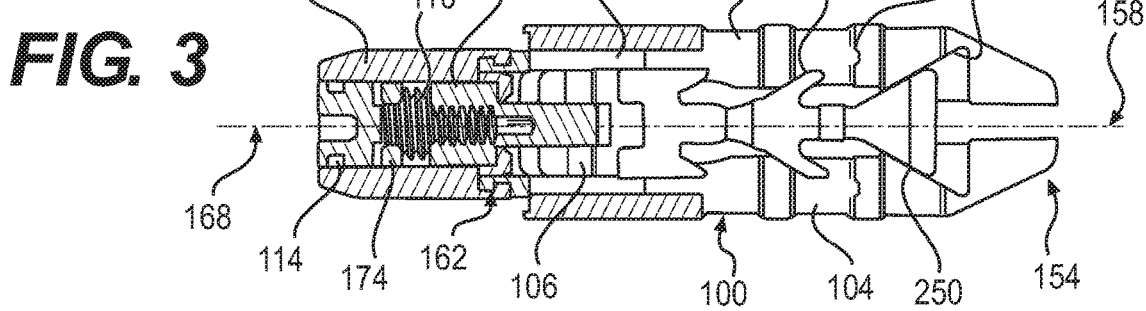
FIG. 3 depicts the cross section of FIG. 2, with the spacer expanded by a separation of endplates.
Figure 4:
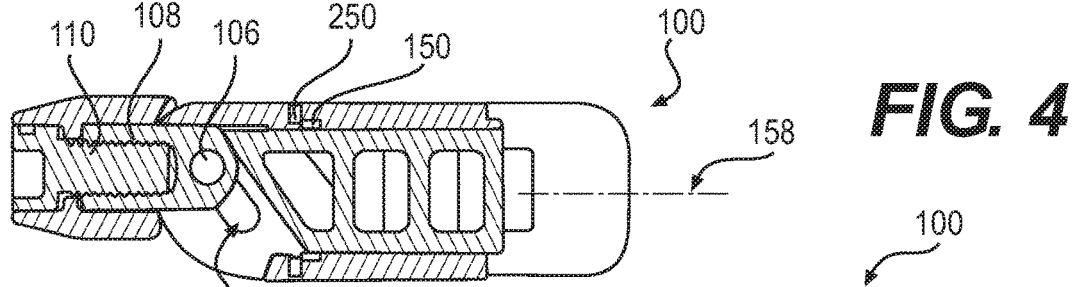
FIG. 4 depicts the spacer of FIG. 3, taken along an orientation 90 degrees offset from the orientation of the spacer of FIG. 3.
Figure 5:
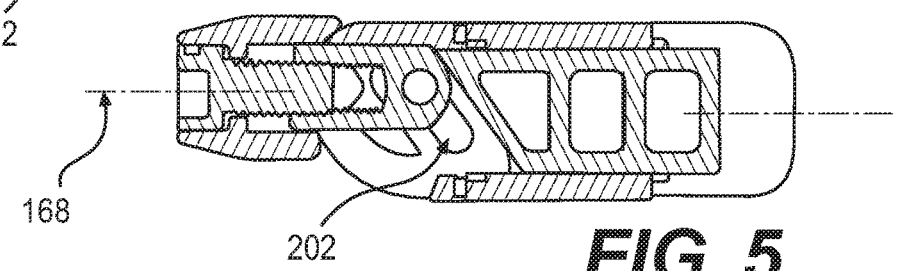
FIG. 5 depicts the spacer of FIG. 2, taken along an orientation 90 degrees offset from the orientation of the spacer of FIG. 2.

With reference to FIGS. 1-3, the disclosure provides an expandable spacer 100 having an adjustable height. The implant is inserted between two adjacent bony surfaces to facilitate separation of the bones, and if desired, to promote the fusion of bony surfaces. Although intended to be useful with any adjacent bony surface in which fusion is desired, the implant is advantageously applied to insertion between two adjacent vertebral bodies in any section of the spine, including the cervical, thoracic, lumbar, and sacral vertebral sections. More than one spacer 100 may be implanted within the body, for example between successive or separated vertebrae, between adjacent vertebrae. The use of multiple implants is particularly advantageous for patients whose back pain is not limited to a localized area, or for patients whose localized damage has progressed to other areas of the spine.

The implant and methods for its insertion can be used in a treatment protocol for any of a wide variety of conditions in a patient involving diseased or damaged bony structures. The patient can be a human being. Additionally, it is contemplated that the implant may be useful in veterinary science for any animal having adjacent bony structures to be fused. The implant can collapse, for example, to approximately one half of an expanded size. When in this collapsed configuration, the implant can be inserted into a space through a small incision and narrow pathways, using appropriate minimally-invasive techniques, and can be positioned within the space between adjacent bones, and there expanded to a desired therapeutic height. The incision may be short, for example about one inch in length, which is smaller than the implant in an expanded configuration. If the desired position and/or expansion are not achieved, the implant can be collapsed, repositioned, and re-expanded in situ.

Although the implant is exemplified herein for use in the spine, the implant is contemplated for fusion of any bony structures. While the implants are described herein using several varying embodiments, the implants are not limited to these embodiments. An element of one embodiment may be used in another embodiment, or an embodiment may not include all described elements.

With reference to FIGS. 1-5, a spacer 100 of the disclosure includes endplates 102, 104 having expansion ramps 150, mateable with moveable lift ramps 250 of a carriage 200. In the embodiment shown, endplates 102, 104 are symmetrical, and spacer 100 can be implanted with either endplate positioned superior with respect to the other. In other embodiments, they may be dissimilar, and a particular orientation may then be advantageous or necessary.

Spacer 100 forms a distal end 154 which is inserted first into the body, and which can be tapered to facilitate insertion between body tissue, and a proximal end 156, to which a tool may be connected. Distal and proximal ends 154 and 156 define a longitudinal axis 158, extending therebetween. To expand spacer 100, lift ramps 250 are displaced relative to endplates 102, 104, causing expansion ramps 150 to slide along lift ramps 250, thereby moving endplates 102, 104 relatively apart, thereby increasing a height of spacer 100. Body tissue engaging projections 152, for example tooth shaped projections, can be provided upon a surface of endplate 102, 104, to further secure spacer 100 in a therapeutic location.

Lift ramps 250 extend from carriage 200, which is slideably retained within a frame 126 extending between endplates 102, 104. Carriage 200 is displaced relative to endplates 102, 104 by being pulled by a pin 106 connected to a link 108 threadably connected to an actuating screw 110. One or more guide elements 112, associated with frame 126, can be provided to prevent endplates 102, 104 from moving along longitudinal axis 158 along with carriage 200, thereby causing lift ramps 250 and expansion ramps 150 to be moved relative to each other, expanding or contracting Spacer 100. Actuating screw can be prevented from moving along longitudinal axis by a blocking flange 114 or 174.

With further reference to FIGS. 6-7, in accordance with the disclosure, an articulating screw support 160 is slideably retained in connection with frame 126 by, in one embodiment, a flanged connection 162. In this manner, a longitudinal axis 168, defined by screw support 160, may form a changeable angle ($\alpha$) with respect to longitudinal axis 158 of endplates 102, 104, or a longitudinal axis of frame 126. Actuating screw is rotatably confined within screw support 160, and is threadably engaged with link 108. Pin 106 pivotally retains link 108 in connection with carriage 200. A slot 202, associated with carriage 200, enables movement of pin 106, whereby pin 106 and link 108 can maintain a fixed orientation with respect to screw support 160, regardless of an angular disposition of screw support 160. Slot 202 is thus configured and dimensioned to enable a location of pin 106, confined therewithin, to correspond to a path of travel of screw support 160 as defined by connection 162.

In one embodiment, a path of travel of screw support 160 is defined by connection 162 to maintain a fixed orientation of carriage 200 with respect to frame 126. More particularly, if screw support 160 is moved along a path which does not pivot about a single point defined by a current location of pin 106, pin 106 may move within slot 202 to maintain a fixed distance in a contracted position between pin 106 and screw support 160, and therefore carriage 200 is not caused to be moved as screw support 160 is moved. In other embodiments, slot 202 is defined to cause a predetermined movement of carriage 200 as screw support 160 is moved.

Similarly, regardless of a given orientation of screw support 160, rotation of actuating screw advances or retards link 108 and pin 106, causing movement of carriage 200 relative to endplates 102, 104. More particularly, slot 202 defines a longitudinal axis 268, which is oriented to lie at a non-perpendicular angle ($\beta$) with respect to longitudinal axis 168 of screw support 160, through a substantial portion of the range of motion of screw support 160. In this manner, once a desired orientation of screw support 160 has been established, rotation of actuating screw 110 causes pin 106 to push or pull along an edge of slot 202, thereby causing movement of carriage 200. If axis 168 and 268 are perfectly perpendicular, it is possible no movement can be caused by threading screw 110; however, as a practical matter, reorienting screw support 160 a very small amount can resolve this theoretical limitation. Carriage 200 is slideably retained by a channel or edge interface 116 formed between carriage 200 and at least one endplate 102, 104, thereby limiting movement of carriage 200 along longitudinal axis 158.

With reference to FIGS. 8-15, an alternative spacer 100A of the disclosure functions in analogous manner to the embodiment of FIGS. 1-7, however in this embodiment, rotation of actuating screw 110A causes carriage 200A to push endplates 102A, 104A to cause expansion. More particularly, an orientation of expansion ramps 150A and lift ramps 250A are oriented 180 degrees with respect to longitudinal axis 158. The embodiment of FIGS. 8-9 additionally illustrates an alternative actuating screw 110A configuration, in which screw 110A is rotatably connected to link 108A, and threadably connected within screw support 160A, whereby screw 110A moves along longitudinal axis 168 within a threaded bore 118A of screw support 160A. Screw 110A causes movement of link 108A, which advances or retards pin 106 within slot 202, to cause a corresponding movement of carriage 200A. As the various aspects of differing embodiments of the disclosure may be substituted where logical, generally, it may be seen that this alternative screw 110A configuration can be used with other embodiments of the disclosure, as well.

As may be seen in FIG. 2, for example, in one embodiment, connection 162 includes interlocking mating flanges 164, 166, associated with frame 126 and screw support 160, respectively. Flanges 164, 166 form mutually curved guide surfaces defining a path of movement for screw support 160 relative to frame 126, and retain screw support 160 in engagement with frame 126. Other configurations are possible, provided screw support 160 and frame 126 may form different angular dispositions with respect to each other, and wherein actuating screw 110 or 110A (FIG. 8) may interact with carriage 200 or 200A to slide carriage 200 or 200A with respect to frame 126, 126A.

Figure 16:
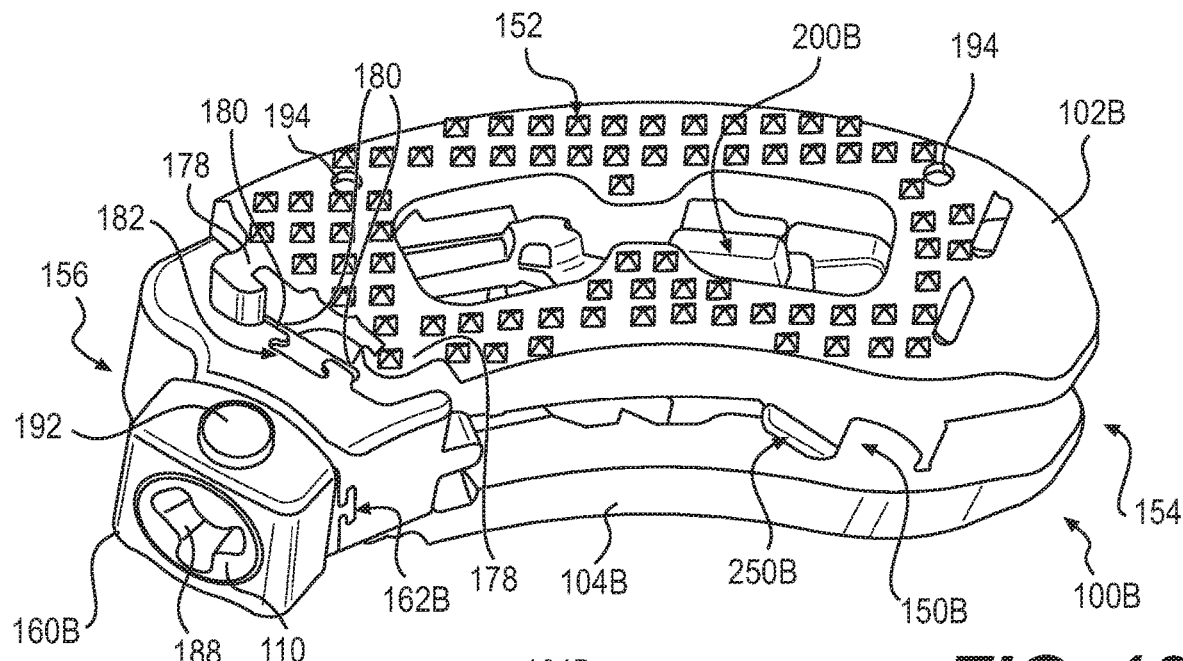
FIG. 16 is a perspective view of an alternative spacer embodiment of the disclosure, having a curved shape.
Figure 17:
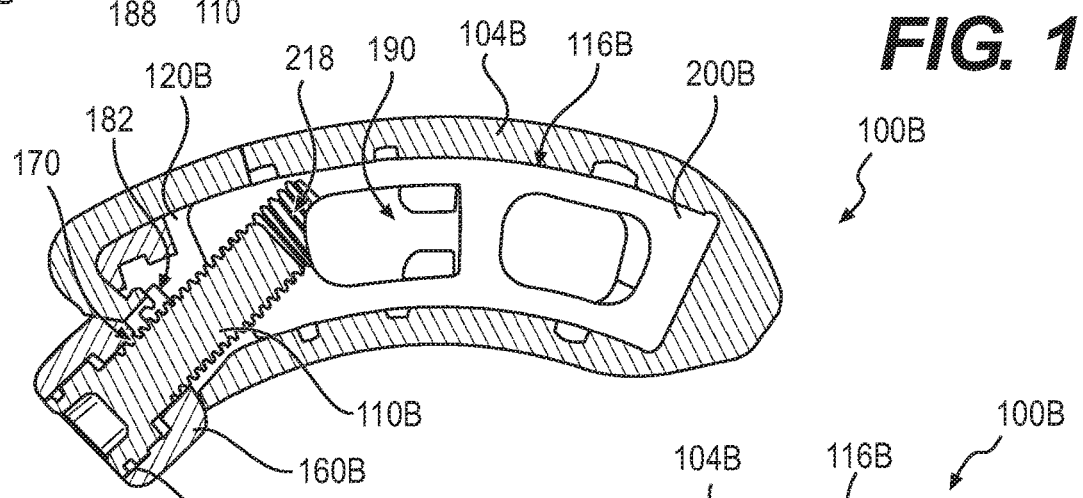
FIG. 17 depicts a cross section of the spacer of FIG. 16, the endplates not separated.
Figure 18:
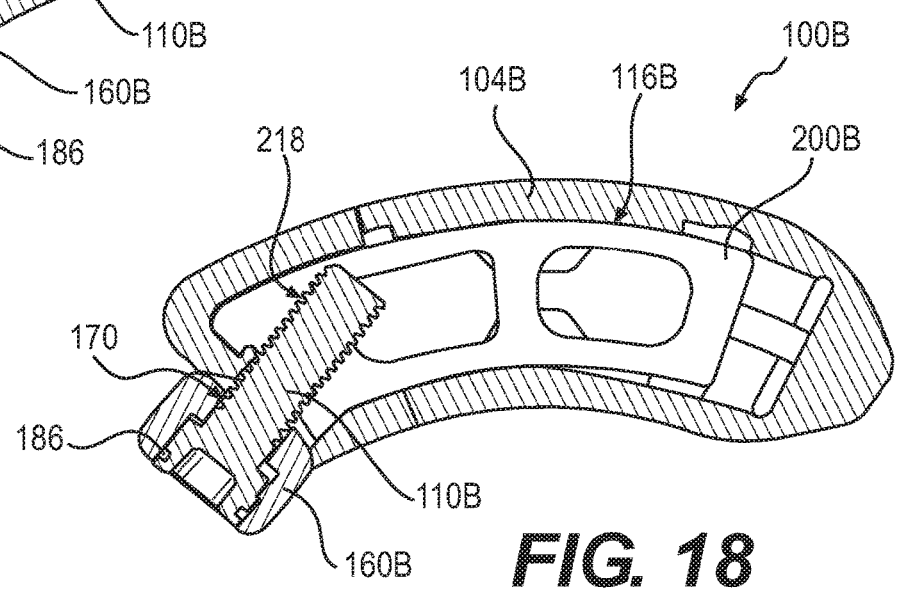
FIG. 18 depicts a cross section of the spacer of FIG. 16.
Figure 19:
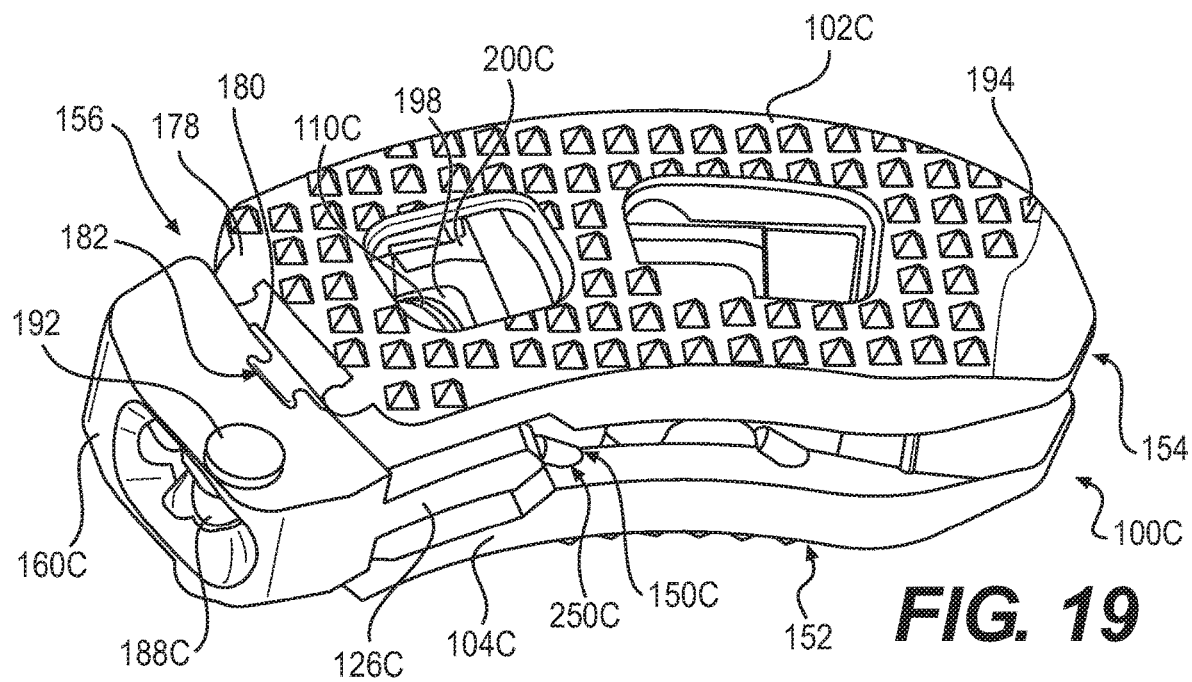
FIG. 19 is a perspective view of an alternative spacer embodiment of the disclosure, the actuating screw secured to the carriage by a nut.

Turning now to FIGS. 16-18, spacer 100B includes curved endplates 102B, 104B, and a curved carriage 200B slideable within edge interface 116B. Carriage 200B includes a threaded bore 218, into which actuating screw 110B is threaded. As screw 110B is rotated in a first direction, carriage 200B is moved towards distal end 154, and as screw 110B is rotated in a second, opposite direction, carriage 200B is moved away from distal end 154. Depending upon the angular direction of ramps 150B and 250B, endplates 102B, 104B are moved together or apart, as described with respect to the embodiments of FIGS. 1 and 8. Spacer 100B forms, overall, a curved shape, which can advantageously be rotated as it is inserted through a minimal incision, to thereby become implanted between adjacent bones. This reduces an extent of a requirement of rotating a spacer, within the body, prior to insertion between the bones, thus reducing an adverse impact to adjacent body tissue.

As actuating screw 110B threads into carriage 200B, shaft 140 and head 142 of screw 110B are angularly displaced with respect to screw support 160B. Accordingly, screw support 160B is provided with a gapped region 170, allowing movement of screw 110B. Additionally, screw support 160B is retained in connection with a frame 126B by a flanged connection 162B, in this case a dovetail connection. Connection 162B enables screw support 160B to be angled with respect to frame 126B, to facilitate access to screw 110B by a tool (not shown), when spacer 100B is implanted within the body, and to further enable screw 110B to change an angle with respect to frame 126B.

Frame 126B is connected to each of endplates 102B, 104B by a flanged connector 176, in this embodiment a dovetail formed between endplate flanges 178 extending from each of endplates 102B, 104B, and frame flanges 180 associated with an intermediate connector 182. Actuating screw 110B can be rotatably retained within screw support 160B by a washer or flange (not shown) positioned in groove 186 within screw support 160B, or intermediate connector 182 can be configured to rotatably retain screw 100B.

With reference to FIGS. 16-18, a spacer 100C functions in a similar manner to spacers 100, 100A, and 100B, with the following distinctions. Initially, in the embodiment shown, screw support 160C does not slide along a flanged connector 162, and is connected to endplates 102C, 104C in a like manner as spacer 100B. However, screw support 160C could be connected to a remainder of spacer 100C using a flange connector 162. Additionally, actuating screw 110C has a tool engagement 188C that is different than the tool engagement of other embodiments, although engagement style 188, or any other style tool engagement, may be provided upon screw 110C. Engagement style 188 allows for articulating between the holder and the implant by pivot point 192.

Figure 20:
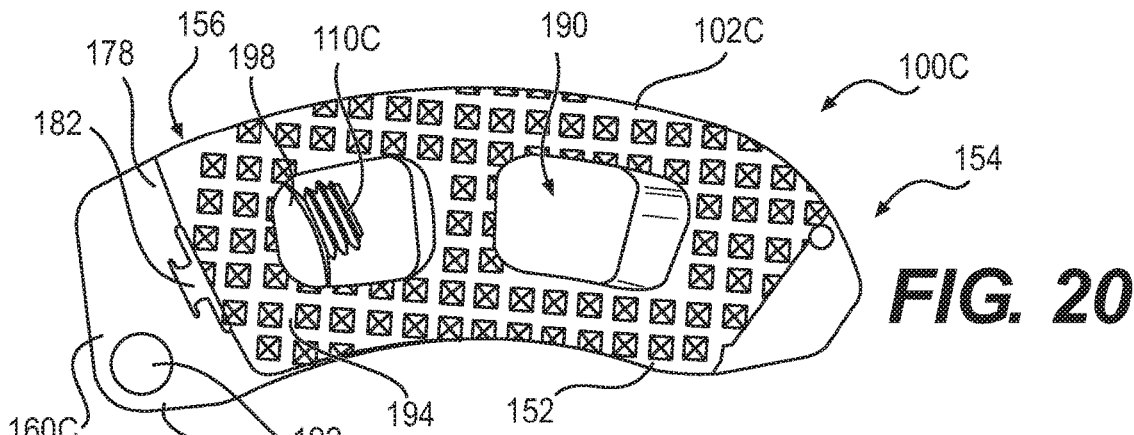
FIG. 20 depicts a top view of the spacer of FIG. 19.
Figure 21:
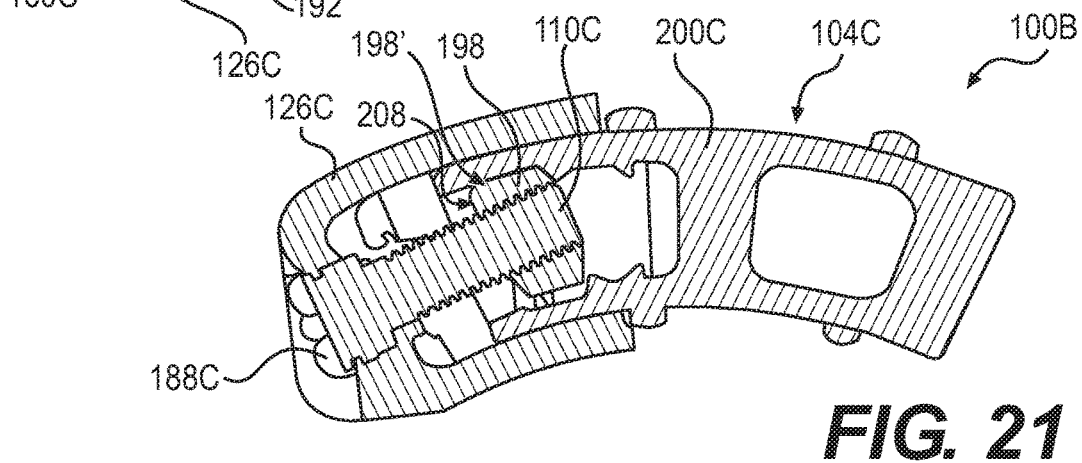
FIG. 21 is a cross section of the spacer of FIG. 19.
Figure 22:
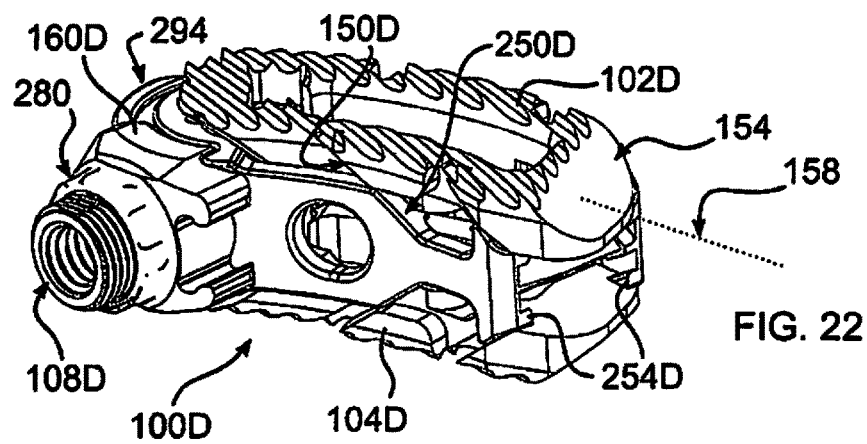
FIG. 22 is a perspective view of an alternative spacer embodiment of the disclosure, having an articulating actuating mechanism, the spacer in an expanded configuration.
Figure 23:
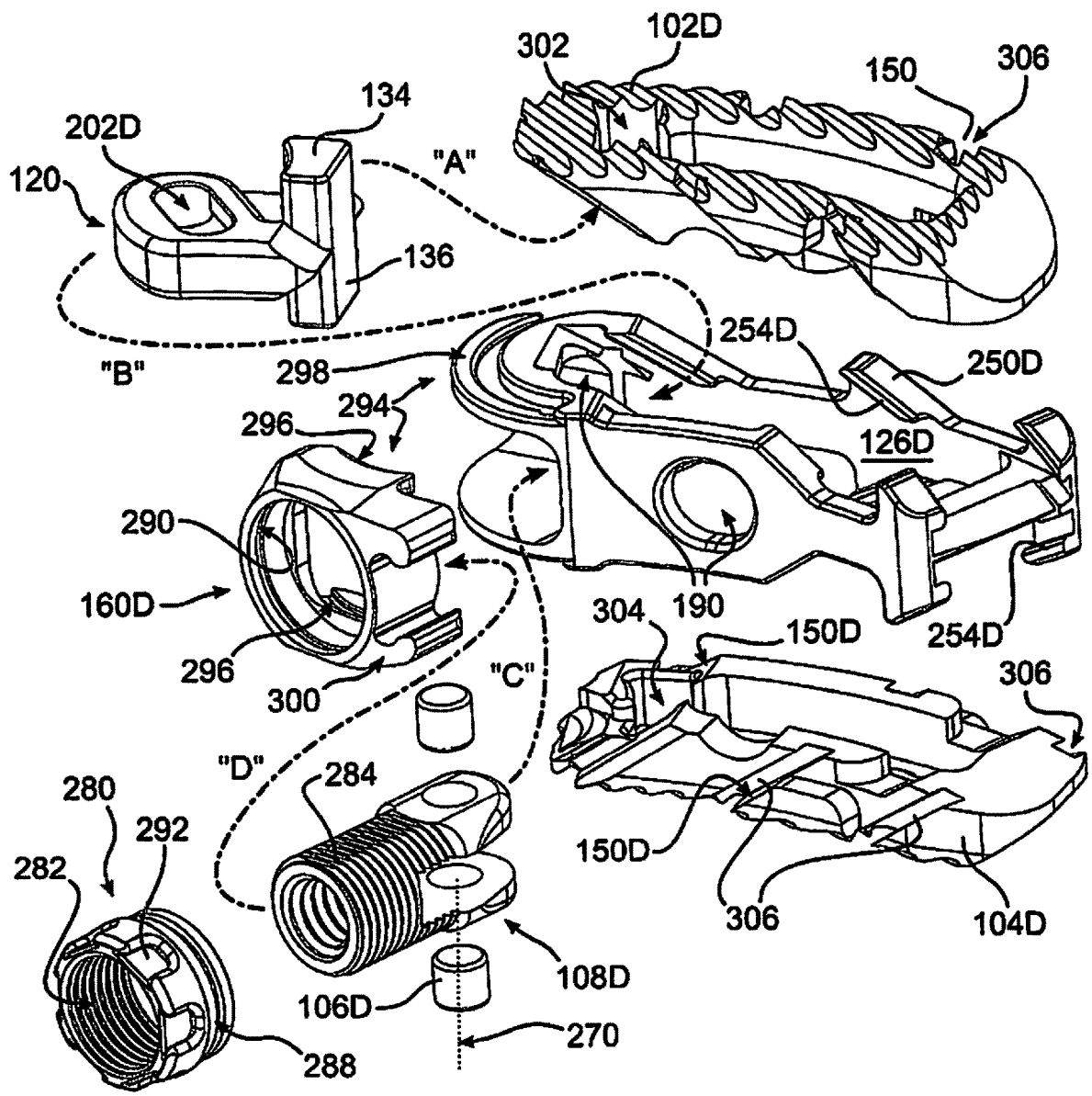
FIG. 23 is an exploded view of the spacer of FIG. 22.
Figure 24:
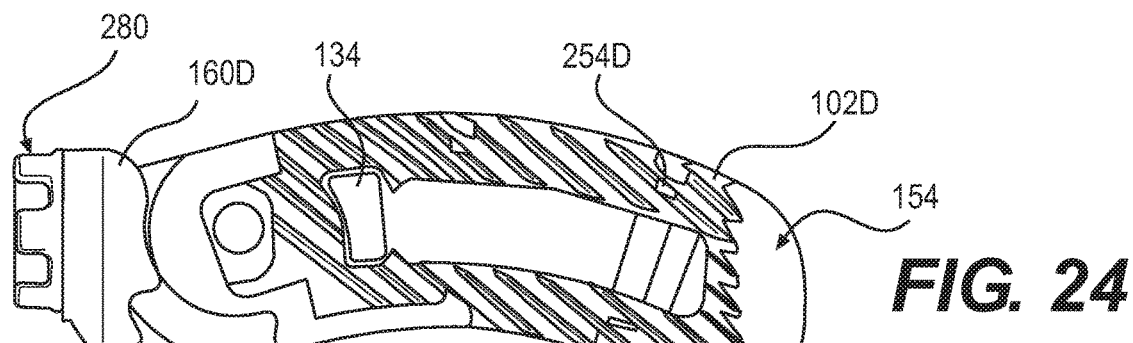
FIG. 24 illustrates the spacer of FIG. 22, in a collapsed configuration, the actuating mechanism aligned with a longitudinal axis of the spacer.
Figure 25:
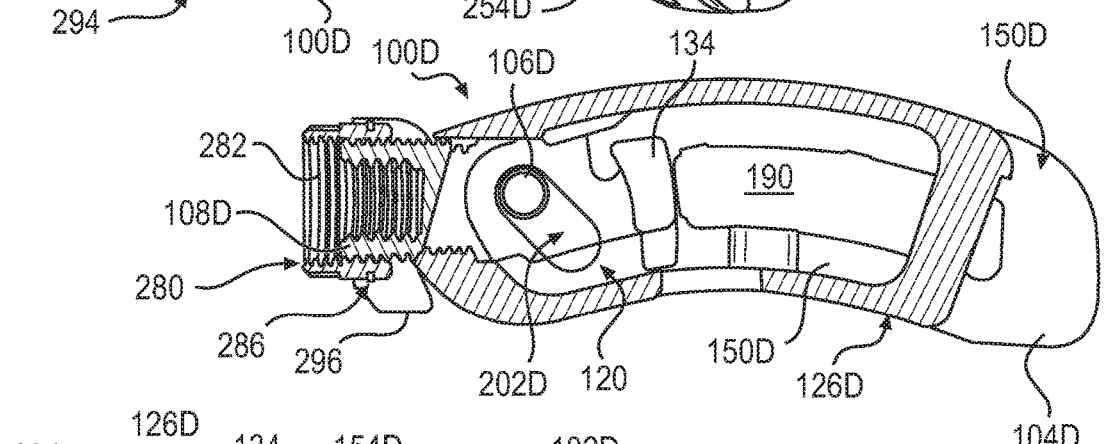
FIG. 25 is a cross-sectional view of the spacer of FIG. 24, taken along a central axis of the spacer.
Figure 26:
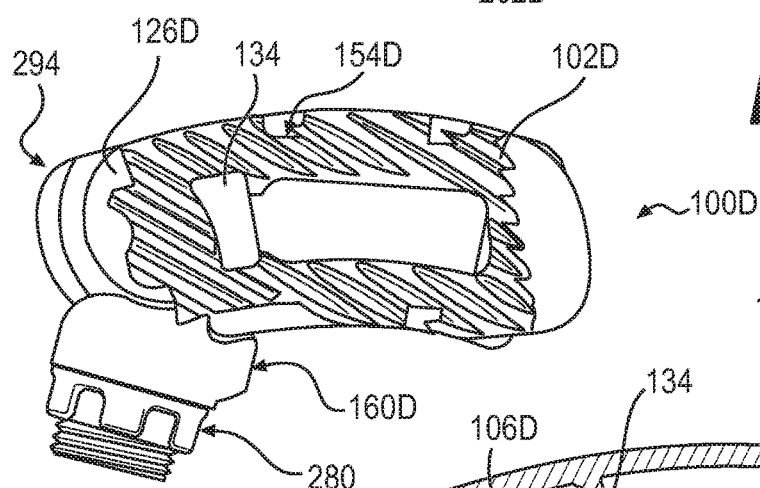
FIG. 26 illustrates the spacer of FIG. 22, in an expanded configuration, the actuating mechanism angled with respect to a longitudinal axis of the spacer.
Figure 27:
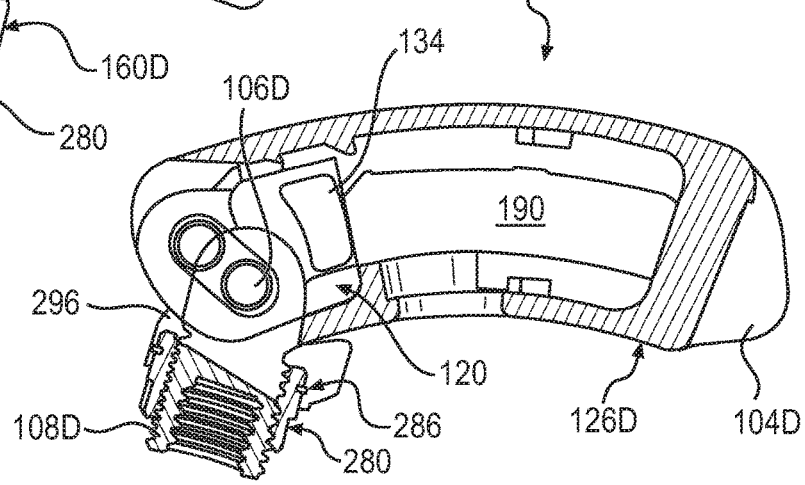
FIG. 27 is a cross-sectional view of the spacer of FIG. 26, taken along a central axis of the spacer.

As may best be seen in FIGS. 20 and 21, nut 198 retains actuating screw 110C in connection with carriage 200C. However, in distinction with respect to threaded bore 218 of spacer 100B, nut 198 may toggle, or change an angular orientation with respect to carriage 200C, as screw 100C is rotated, and carriage 200C is moved. Nut 198 can be provided with a nut bearing surface 198', which mateably interacts with a carriage bearing surface 208. Similar bearing surfaces 198" and 208' can be provided on an opposite side of nut 198, for pushing carriage 200C in an opposite direction. In the embodiment shown, threading nut 198 in the direction of proximal end 156 causes an expansion or increase in height of spacer 100C, and threading nut 198 in a direction of distal end 154 causes a reduction, or decrease in height of spacer 100C. However, ramps 150C and 250C can be oriented to cause an opposite effect.

The following discussion pertains to all embodiments of the disclosure, including spacers 100, 100A, 100B, 100C, 100D, and 100E. For brevity, the letter suffix designating variations of like parts will be omitted, unless a specific distinction is made. For all spacer 100 embodiments of the disclosure, carriage 200 (if present) can be slid, or actuated, when screw support 60 is disposed at an angle with respect to the carriage. In the embodiments of FIGS. 1-15, this angle may vary between 0° and 70°, and with modifications, this angle could be increased to a theoretical maximum approaching 180°. The embodiment of FIGS. 16-18 accomplishes disposing screw 100B at an angle to the endplate bodies by curving the endplates, and by configuring bore 218 at an angle with respect to carriage 200B.

In all embodiments, head 142 of screw 110 (if present) may be accessed by a driving tool extending from outside the body, into the body, while endplates 102, 104 lie at an angle, for example perpendicular, to a pathway into the body. More particularly, spacers 100 of the disclosure may be inserted between vertebral bodies when in a collapsed or non-expanded state, from a lateral approach to the spine. As spacer 100 is inserted between endplates, it is rotated to contact cortical bone of the endplates, and to avoid anatomical structures which should not be disturbed.

Once rotated into position, screw support 60 (if present) can be turned towards an exterior of the body, if it has not already been so turned, whereby a tool may be conveniently mated with a tool engagement 188 of screw head 142. After screw 110 is rotated, endplates 102, 104 separate, expanding or increasing a height of spacer 100, and restoring and maintaining a therapeutic spacing between adjacent bones. In some embodiments, after expansion of spacer 100, screw support 160 may slid along flanged connection 162 to lie at an optimal orientation with respect to body tissue, for example 0 degrees with respect to carriage 200, or at an angle deemed best by the medical practitioner.

Spacers 100 may include ramps 150, 250 of differing height within a spacer, whereby endplates 102, 104 mutually separate at different rates at distal and proximal ends 154, 156, or at sides transverse to distal and proximal ends 154, 156, whereby an angular disposition of adjacent bones may be changed, for example to correct lordosis or scoliosis. Endplates 102, 104 may additionally, or alternatively, be resilient, so that they may conform to bony surfaces, forming a more stable support platform. Accordingly, endplates 102, 104 can be fabricated from a polymeric material, a naturally resilient material, or a resilient metal, for example a shape memory alloy, or any other resilient biocompatible material of sufficient strength and durability for separating bones within the body. Spacers 100 may further be removed or repositioned during an initial implantation procedure, or later in time.

Referring now to FIGS. 22-38, in an alternative embodiment, in which like numbers correspond to like elements in other embodiments herein, a spacer 100D of the disclosure includes a frame 126D having lift ramps 250D slidingly engageable with expansion ramps 150D of endplates 102D, 104D. Drive link 120 is engaged with endplates 102D, 104D, and is configured to pull and displace endplates 102D, 104D with respect to frame 126D, to thereby cause expansion ramps 150D to slide along lift ramps 250D. Accordingly, endplates 102D, 104D move relatively apart along an axis which is transverse to longitudinal axis 158, to increase a height of spacer 100D. In this embodiment, spacer 100D does not include a carriage 200 which is displaced with respect to a frame 126, as is disclosed elsewhere herein, but rather displaces endplates 102D, 104D with respect to a ramped frame 126D. Arrow "A" indicates an orientation of link 120 with respect to endplate 102D, and arrow "B" indicates an orientation of link 120 with respect to frame 126D.

As may be seen in the embodiment of spacer 100D, and other embodiments herein, expansion ramp 250D includes a sliding flanged connection including a side projecting edge 254D which engages a mating channel 306 within endplate 102D or 104D. In this manner, endplates 102D, 104D are retained in connection with frame 126D throughout an extent of separation of endplates 102D, 104D. It should be understood, however, that the endplate 102D or 104D can include a side projecting edge 254D, and the frame can include a channel 306.

Link 120 includes endplate engaging projections 134, 136 which engage corresponding openings 302, 304 in endplates 102D, 104D, respectively. Endplate engaging projections 134, 136 pass through a central opening 190, thereby enabling link 120 to move along axis 158, which axis may be non-linear for curved embodiments, including spacer 100D. In the embodiment shown, link 120 pulls endplates 102D, 104D to expand spacer 100D; however, it should be understood that link 120 could alternatively operate to expand spacer 100D by pushing endplates 102D, 104D, for example if ramps 150, 250D had reversed angles, and projections 134, 136 positively engaged endplates 102D, 104D along axis 158.

Link 120 and endplates 102D, 104D move together with respect to frame 126D, as spacer 100D is expanded or collapsed. Link 120 is pivotally engaged with an actuating screw having the form of a threaded clevis link 108D, to pivot about an axis 270 extending from endplate 102D to endplate 104D, and substantially perpendicular to longitudinal axis 158. Pin 106D passes through slot 202D in link 120. In the embodiment shown in FIG. 23, pin 106D is provided in segments, but could alternatively be a unitary pin.

Nut 280 includes internal threads 282 which mate with external threads 284 of link 108D. Nut 280 is rotatably retained in fixed axial orientation within articulating screw support 160D. In an embodiment, a compressible ring 286 (visible in FIGS. 25 and 27), is positioned in part within a channel 288 within nut 280, and in part within a channel 290 within support 160D. Nut 282 includes tool engaging portions 292 sized and dimensioned to cooperate with a tool (not shown) configured to mate to engaging portions and rotate nut 280 with respect to link 108D, which is prevented from rotation through connection with link 120. Accordingly, as nut 282 is rotated, link 108D is advanced or withdrawn with respect to frame 126D.

Articulating screw support 160D slideably attaches to frame 126D through a curved flanged or dovetail connection 294, which is formed between support dovetail portion 296, and frame 126D dovetail portion 298. The curved connection enables support 160D to be positioned for actuation of nut 280 at an angle with respect to a longitudinal axis of spacer 100D. In this manner, spacer 100D may be inserted into the body along a non-linear path, for example during a transforaminal, posterior, and/or lateral insertion, and support 160D may be positioned to be more readily accessible along the insertion path to a tool end which engages nut 282 for rotation, thereby minimizing disturbance of body tissue. Arrow "C" indicates an orientation of link 108D with respect to frame 126D, and arrow "D" indicates an orientation of link 108D with respect to support 160D.

In addition, slot 202D enables actuating support 160D to be translated along a path defined by dovetail portion 298, without substantially changing a height of spacer 100D. More particularly, a change in location of link 108D due to translation along the path does not cause movement of endplates 102D, 104D, because pin 106D may translate or pivot within slot 202D, thereby not causing movement of link 108D. However, in any position of actuating support 160D along the path, nut 280 may be rotated to displace link 108D, regardless of a location of pin 106D, to change a height of spacer 100D.

Once support 160D is positioned angularly, dovetail connection 294 secures support 160D with respect to frame 126D, whereby rotation of nut 280 causes links 108D and 120 to move with respect to frame 126D, thereby moving endplates 102D, 104D with respect to frame, causing an expansion or contraction of a height of spacer 100D.

Articulating screw support 160D further includes a tool engaging connector 300 sized and dimensioned to slidingly engage a mating tool end (not shown). In the embodiment shown, connector 300 is a dovetailed connector, although other tool engagement types or shapes can be used, as would be understood within the art. In this manner, spacer 100D may be manipulated into position within the body, and support 160D may be moved to be disposed at a desired angle with respect to an entry path of spacer 100D into the body.

Spacer 100D, as well as other spacer embodiments of the disclosure, can be inserted at a collapsed height transforaminally, for example, and are capable of articulating into anterior placement. Once placement is achieved, the implant is capable of expanding for disc height restoration. Additionally, the implant can be positioned anteriorly, and can be expanded through a continuous range to provide axial balance and greater endplate contact area. Additionally, spacers of the disclosure allow for superior sagittal correction, through the use of a relatively smaller insertion window, decreasing the need for boney damage. Thus, spacers of the disclosure provide the benefits of an ALIF device through a familiar posterior approach, decreasing surgery time and associated blood loss, as well as eliminating the need for an access surgeon.

Figure 39:
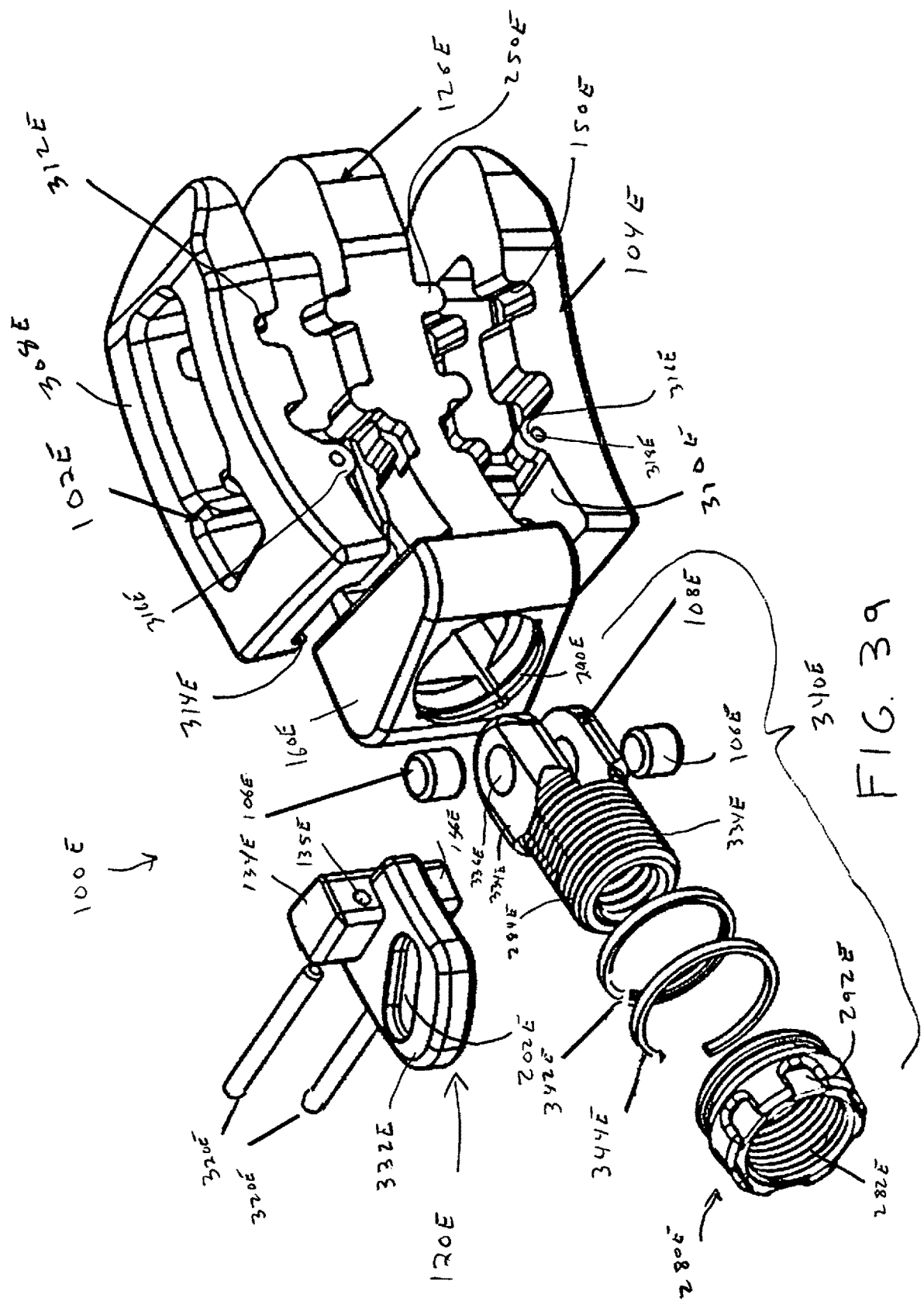
FIG. 39 is an exploded view of an alternative space embodiment of the disclosure.

Referring now to FIG. 39, in an alternative embodiment, in which like numbers correspond to like elements in other embodiments herein, a spacer 100E is illustrated. In the illustrated embodiments, spacer 100E includes a frame 126E engaged with endplates 102E, 104E. In some embodiments, the frame 126E includes lift ramps 250E slidably engaged with expansion ramps 150E of endplates 102E, 104E. A drive link 120E may be engaged with endplates 102E, 104E and may be configured to pull and displace endplates 102E, 104E with respect to frame 126E, to thereby cause expansion ramps 150E to slide along lift ramps 250E. Accordingly, the spacer 100E may open as the endplates 102E, 104E move relatively apart along an axis, which is transverse to longitudinal axis (FIG. 40), to thereby increase height of spacer 100. In this embodiment, the endplates 102E, 104E are pivotally coupled to the drive link 120E. As the endplates 102E, 104E are displaced by the frame 126E, the endplates 102E, 104E pivot at the drive link 120E so that the spacer 100E is moveable from a collapsed configuration to an open configuration.

Figure 40:
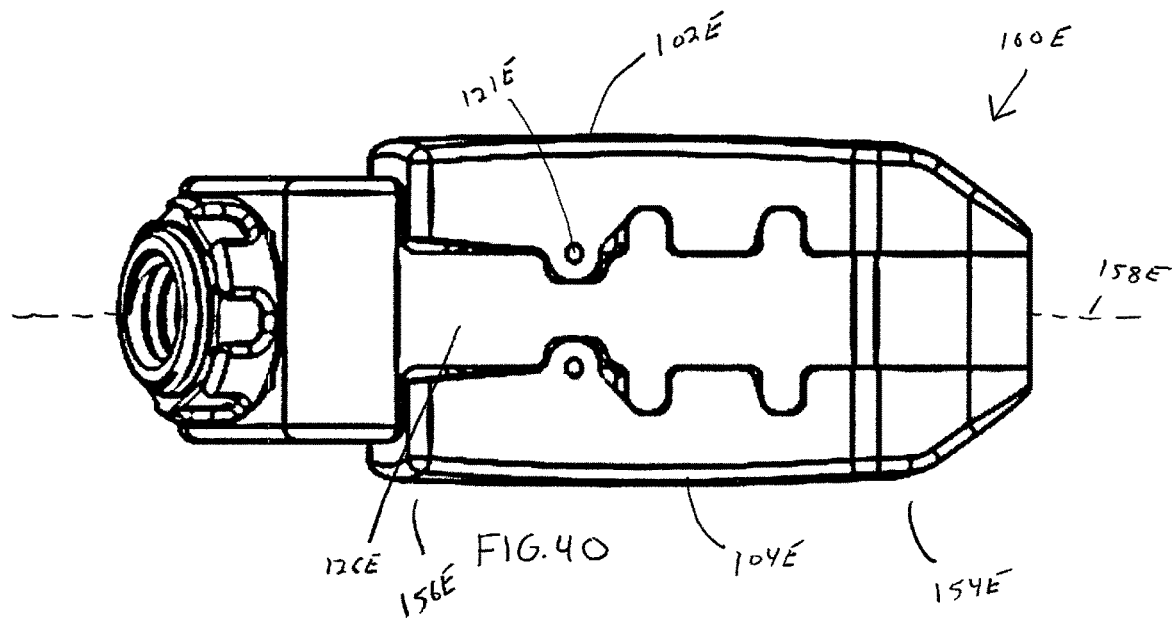
FIG. 40 is a side view of the spacer of FIG. 39 in a collapsed configuration.
Figure 41:
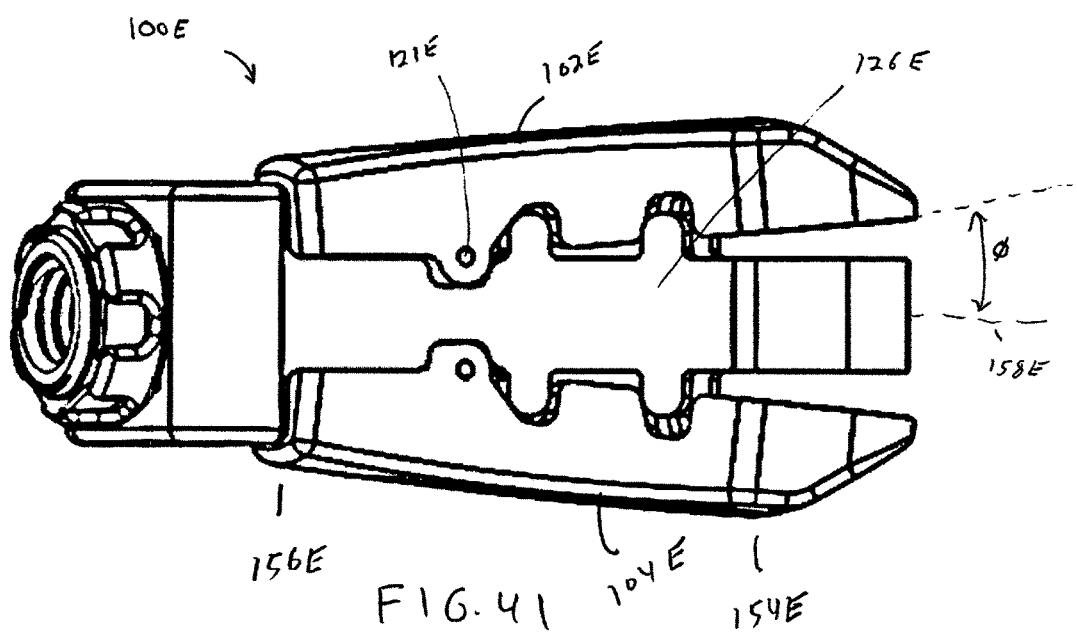
FIG. 41 is a side view of the spacer of FIG. 39 in an open configuration.

With additional reference to FIGS. 40 and 41, opening of spacer 100E is illustrated in more detail in accordance with example embodiments. FIG. 40 illustrates spacer 100E in a closed configuration. As previously described, drive link 120E may be used to pull and displace endplates 102E, 104E with respect to frame 126E. In the illustrated embodiment, one end (e.g., proximal end) of the endplates 102E, 104E is pivotally coupled to the drive link 120E causing the spacer 100E to open as the endplates 102E, 104E move relatively apart. FIG. 41 illustrates spacer 100E in an open configuration. When open, the distal end 154E of the spacer 100E may have a height that is generally greater than the proximal end 156E of the spacer 100E. Accordingly, the spacer 100E may be opened after implantation to achieve a lordotic angle, which may for example, be used to correct lordosis or scoliosis. The lordotic angle θ may vary, for example, from 0° to 12° for a cervical application, although much different values may be advantageous for other joints. Lordotic angles may also be achieved, for example, by shaping one or both endplates 102E, 104E to have relatively non-coplanar surfaces, in addition to pivoting of the endplates 102E, 104E.

Figure 43:
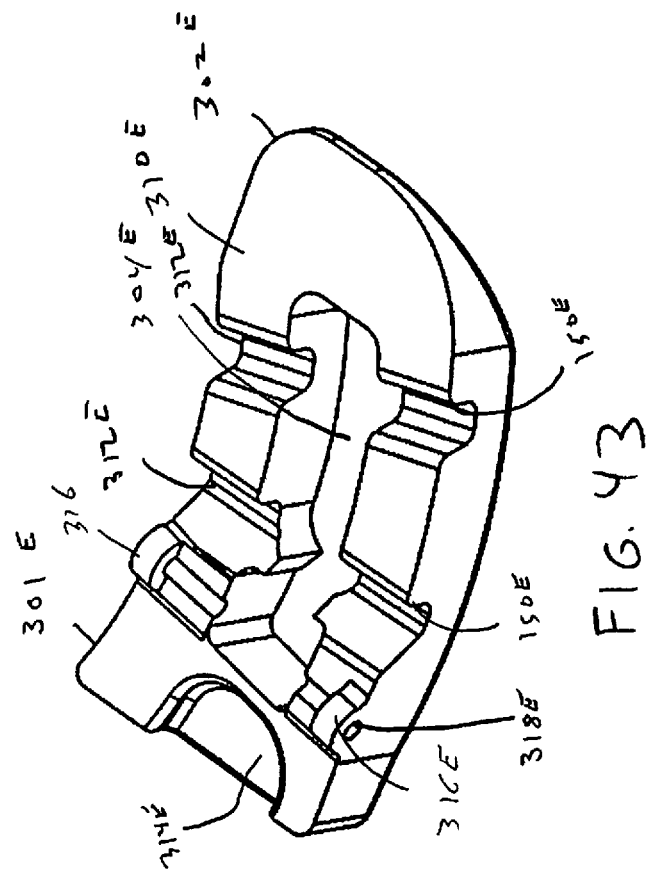
FIGS. 42 and 43 are alternative views of an endplate of the spacer of FIG. 39.
Figure 42:
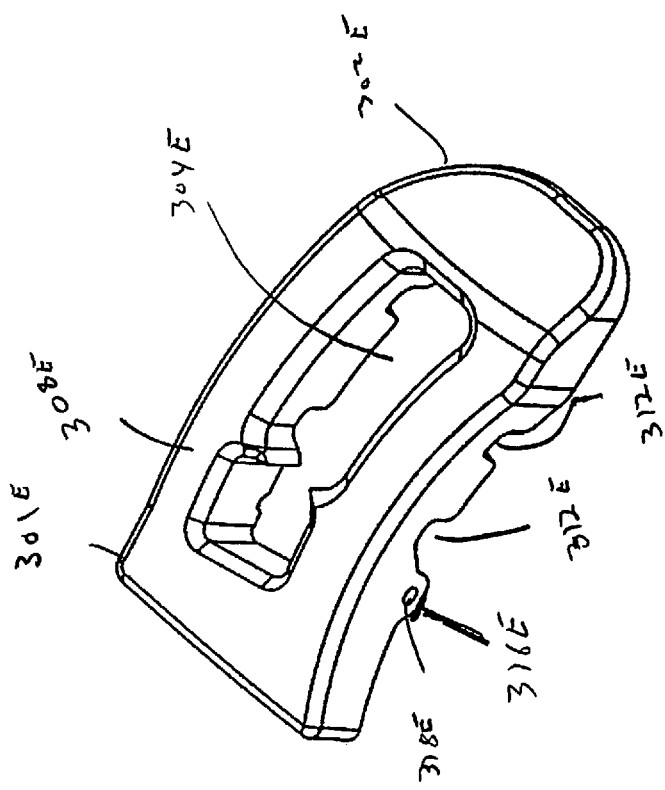

Embodiments of endplates 102E, 104E will now be described in more detail with additional reference to FIGS. 42 and 43. The following description is for endplate 102E; however, it should be understood that endplates 102E and 104E may be symmetrical so the description may equally apply to endplate 104E. Endplate 102E may have a proximal end 301E and a distal end 302E. In an embodiment, the endplate 102E may further comprise a through opening 304E. The through opening 304E, in an exemplary embodiment, may be sized to receive bone graft or similar bone growth inducing material and further allow the bone graft or similar bone growth inducing material to be packed in a central opening 306E in the frame 126E.

As illustrated, endplate 102E may further comprise an outer facing surface 308E connecting proximal end 301E to distal end 302E, and an inner facing surface 310E connecting proximal end 301E to distal end 302E. Grooves 312E may be formed in inner facing surface 310E. In the illustrated embodiment, expansion ramps 150E of the endplate 102E may be formed in the grooves 312E. As previously described, the expansion ramps 150E may engage corresponding lift ramps 250E of frame 126E. As best seen in FIG. 43, endplate 102E may further comprise a cutout 314E in proximal end 301E. Cutout 314E may be sized to receive threaded clevis link 108E.

Endplate 102E may further include a pair of ear portions 316E. As best illustrated on FIG. 43, the ear portions 316E may be disposed one each side of the endplate 102E. The ear portions 316E may each include an aperture 318E. The aperture 318E may define a pivot axis about which the endplate 102E may be selectively rotated. A pivot pin 320E (e.g., shown on FIG. 39) may pass through each of the apertures 318E in endplate 102E to pivotally couple the endplate 102E and drive link 120E. As best seen in FIG. 39, the pivot pin 320E may pass through a corresponding opening in engaging projection 134E of drive link 120E. While pivot pin 320E is illustrates a being a unitary pin, alternative embodiments of pivot pin 320E may be segmented, e.g., comprised of one or more parts.

Embodiments of frame 126E will now be described with additional reference to FIG. 44. As illustrated, frame 126E may include a proximal end 322E and a distal end 324E. Side portions 326E, 328E may connect proximal end 322E and distal end 324E. Proximal end 322E, distal end 324E, and side portions 326E, 328E may define central opening 306E. As previously described, frame 126E may further comprise lift ramps 250E. In the illustrated embodiment, lift ramps 250E may be disposed on side portions 326E, 328E. As illustrated, frame 126E may further comprise a guide slot 330E for drive link 120E in at least one of side portions 326E, 328E. In some embodiments, proximal end 322E of frame 126E may further comprise screw support 160E. In contrast to the preceding embodiment illustrated on FIG. 23, screw support 160E may be integrally formed with frame 126E as illustrated on FIG. 44.

Figure 45:
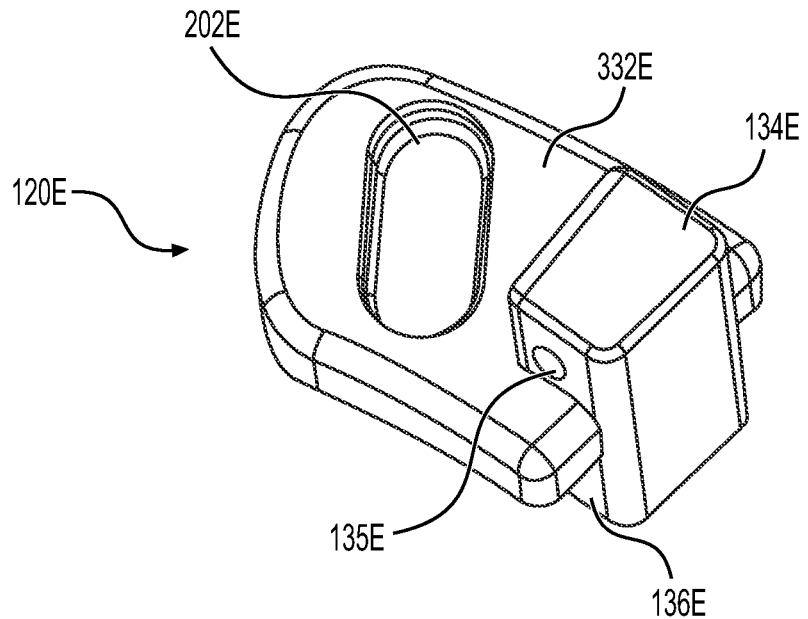
FIG. 45 illustrates the drive link of the spacer of FIG. 39.

Embodiments of drive link 120E will now be described with additional reference to FIG. 45. As illustrated, drive link 120E may include a body portion in the form of plate 332E. Slot 202E may be formed in plate 332E. Drive link 120E may further include engaging projections 134E, 136E that engage endplates 102E, 104E. As previously described, engaging projections 134E, 136E may each include an opening 135E through which pivot pin 320E (best seen n FIG. 46) may pass to pivotally couple drive link 120E and endplates 102E, 104E. Engaging projections 134E, 136E may pass through central opening 306E in frame 126E. In the illustrated embodiment, drive link 120E may operate to pull endplates 102E, 104E causing the endplates to expand while pivoting about pivot pin 320E. Alternatively, drive link 120E may operate to push endplates 102E, 104E causing endplates to collapse while pivoting about pivot pin 320E. Alternate designs may also cause drive link 120E to operate in an opposite manner with pulling of endplates 102E, 104E to cause collapsing while pushing may cause expansion with resultant opening of spacer 100E.

In some embodiments, drive link 120E and endplates 102E, 104E may move together with respect to frame 126E, as spacer 100E is expanded or contracted. Drive link 120E may be pivotally engaged with an actuating screw, for example, having the form of threaded clevis link 108E, best seen on FIG. 39. Threaded clevis link 108E may include screw portion 334E and head portion 336E. Screw portion 334E may include threads 384E. Head portion 336E may be in the form of a clevis, as illustrated on FIG. 39. Pin 106E may pass through openings 338E in head portion 336E and pass through slot 202E in drive link 120E to secure drive link 120E and clevis link 108E. In the embodiment shown in FIG. 39, pin 106E may be segmented but alternative embodiments may include use of a unitary pin.

Figure 46:
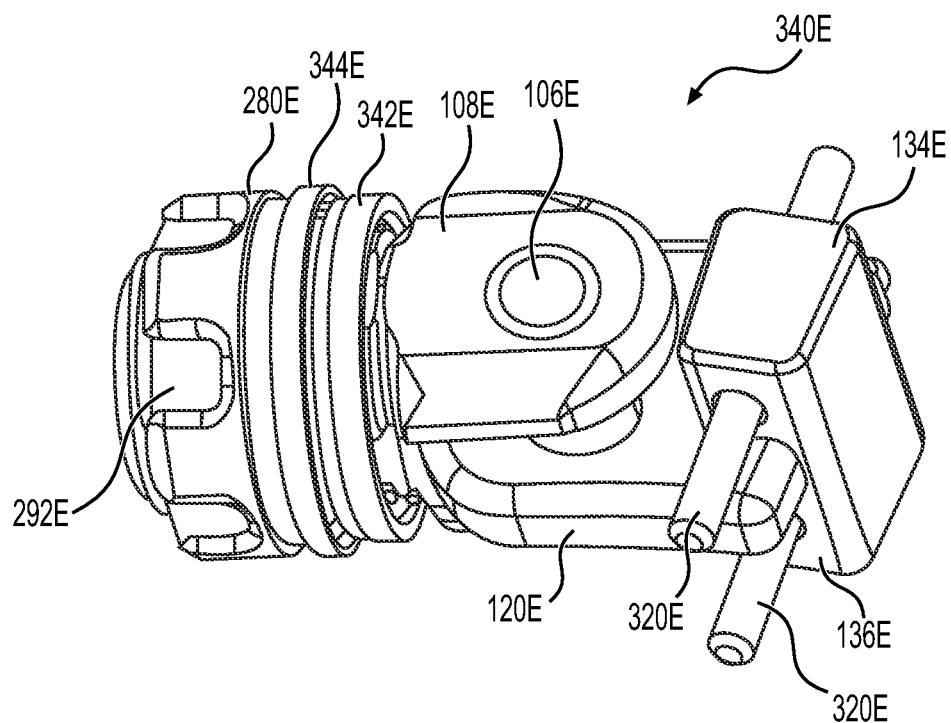
FIG. 46 is a perspective view illustrating an actuation subassembly of the spacer of FIG. 39.

With additional reference to FIG. 46, actuation subassembly 340E will now be described in accordance with embodiments of the present invention. Actuation subassembly 340E may include nut 280E, threaded clevis link 108E, and drive link 120E. As previously described, pin 106E may secure drive link 120E and clevis link 108E. Nut 280E may include internal threads 282E (best seen on FIG. 39) that may mate with corresponding external threads 284E of threaded clevis link 108E. Ring 342E and washer 344E may also be disposed on nut 280E. Ring 342E may be configured to be disposed in a channel 290E in screw support 160E. Nut 280E may include tool engaging portions 292E dimensions to cooperate with a tool (not shown) configured to mate with tool engaging portions 292E and rotate nut 280E with respect to link 108E. As nut 280E is rotated, link 108E may be advanced or withdrawn with respect to frame 126E.

Figure 47:
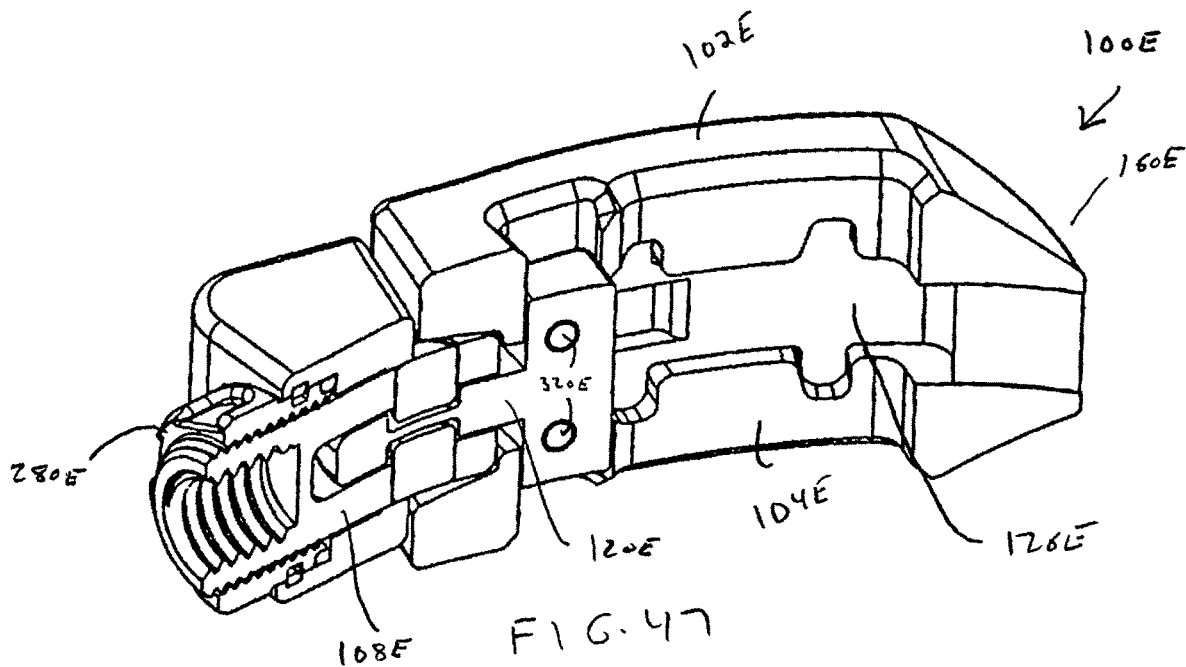
FIG. 47 is a cutaway view illustrating the spacer of FIG. 39 in a collapsed configuration.
Figure 48:
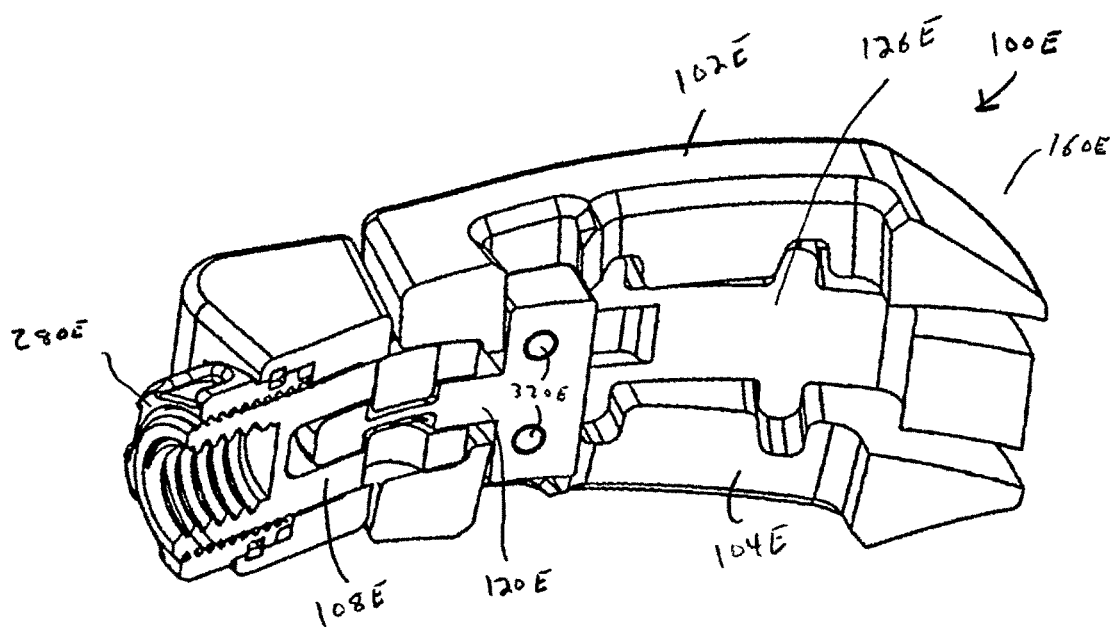
FIG. 48 is a cutaway view illustrating the spacer of FIG. 39 in an open configuration.
Figure 4A:
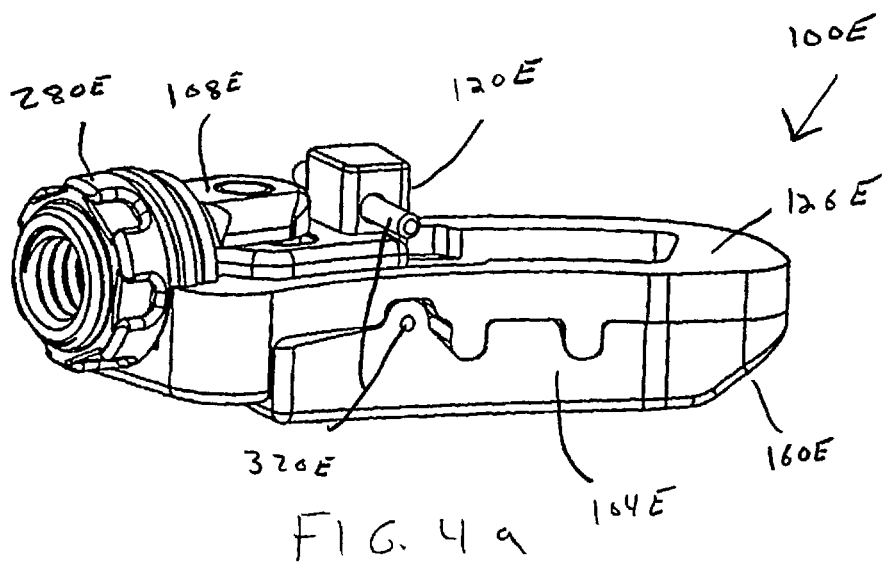
Figure 5B:
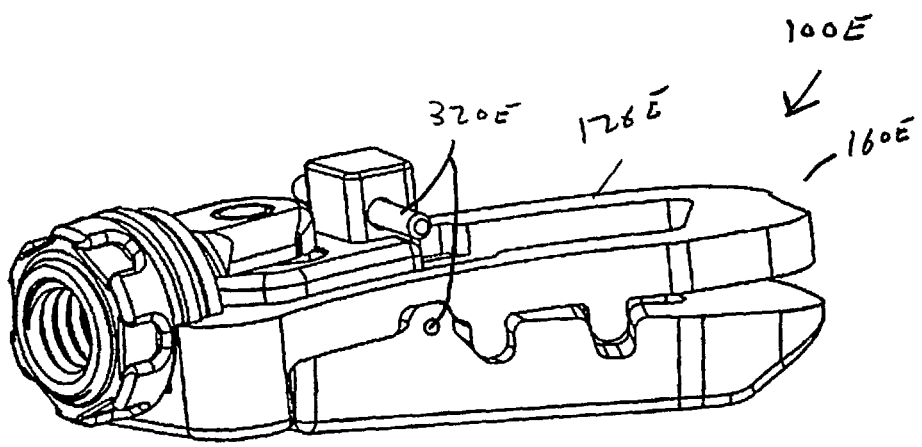

With additional reference to FIGS. 47-50, opening of spacer 100E is illustrated in more detail in accordance with example embodiments. FIG. 47 illustrates spacer 100E in a closed configuration. FIG. 48 illustrates spacer 100E in an open configuration. FIGS. 47-50 are cutaway views with portions of spacer 100E removed to illustrate internal components. In FIGS. 49 and 50, plate 102E has been removed. To actuate spacer 100E, nut 280E may be rotated. Rotation of nut 280E should cause clevis link 108E to either advance or withdraw with respect to frame 126E. As previously described, clevis link 108E and drive link 120E may be coupled such that advancement or withdrawal of clevis link 108E should cause corresponding movement of drive link 120E. As drive link 120E is advanced, drive link 120E may pull and displace endplates 102E, 104E with respect to frame 126E. Endplates 102E, 104E may be displaced such that expansion ramps 150E of endplates 102E, 104E, engage lift ramps 250E of frame 126E. In other words, endplates 102E, 104E may be displaced and driven along lift ramps 250 to cause the endplates 102E, 104E to move relatively apart and open at distal end 160E of spacer 100E. Because endplates 102E, 104E and drive link 120E are pivotally coupled, the endplates may rotate about pivot point (e.g., at pivot pins 320E). In this manner, a lordotic angle may be introduced to spacer 100E after implantation.

With respect to all embodiments, in accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Spacers 100 of the disclosure form a smaller dimension during implantation, relative to a final dimension for spacing bones. Accordingly, nerve roots can be visualized and avoided during insertion, and nerve root manipulation can be avoided or minimized.

As spacers 100 of the disclosure can be articulated during implantation, they can be inserted between bones by being passed through a minimally invasive entry, for example through an incision approximating the smallest collapsed dimension, for example transverse to a longitudinal dimension extending between distal and proximal ends 154, 156. This enables exceptional anterior placement without impaction, as well as facilitating implantation from other approaches. Implants of the disclosure further develop a good bone contact area, as an implant with a larger footprint may be inserted through a reduced size incision, due to the overall dimensions of the implant being reduced during insertion.

Spacers 100 of the disclosure enable a continuous expansion and retraction over a range of displacements according to predetermined dimensions of a specific spacer design. This provides the ability to distract vertebral bodies or other bones to a desired height or separation. Endplates 102, 104 can be shaped to form planes or surfaces which converge relative to each, to provide for proper lordosis, and can be provided with openings 190 through which bone may grow, and into which bone graft material may be placed. Spacers 100 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Spacers 100 of the disclosure may be further secured in connection with the body by passage of elongated fasteners through frame 162, or an endplate 102, 104. As described therein, a blocking mechanism can be used to prevent backing out of the elongated fastener. Similarly, screw 110 can be provided with a blocking mechanism as described in the foregoing reference, or a resilient washer (not shown) may be positioned within groove 186, to resist unintended rotation of screw 110.

Implants of the disclosure may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; stainless steel, polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

Spacers 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of spacers 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the implants of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Spacers 100 may be implanted within any level of the spine, and may also be implanted in other joints of the body, including joints of the hand, wrist, elbow, shoulder, hip, knee, ankle, or foot.

In accordance with the invention, a single spacer 100 may be used, to provide stabilization for a weakened joint or joint portion. Alternatively, a combination of two, three, or more of any of spacer 100 may be used, at a single joint level, or in multiple joints. Moreover, implants of the disclosure may be combined with other stabilizing means.

Additionally, spacers 100 of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of an implant of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position spacer 100 may be performed through an Anterior, Anterolateral, Posterolateral, Lateral, or any other approach.

In a typical embodiment, spacer implants of the disclosure have an uncompressed height, before insertion, of 7 to 13 mm, and may advantageously be provided in cross-sections of 10×26 mm, 12×31 mm and 12×36 mm, with 4, 8, 12, or 16 degree lordotic angles, although these are only representative sizes, and substantially smaller or larger sizes can be therapeutically beneficial. In one embodiment implants in accordance with the instant disclosure are sized to be inserted using an MIS approach, for example using a reduced incision size, for example less than about 5 cm, and advantageously less than about 2.5 cm, with fewer and shorter cuts through body tissue. Spacer 100 may advantageously be used in combination with other known or hereinafter developed forms of stabilization or fixation, including for example rods and plates.

Spacer implants of the disclosure can be inserted into the body, advantageously in a collapsed or non-expanded configuration, through a transforaminal approach, and can articulate in attachment to an inserter tool (not shown), for example for anterior placement. Once placement is achieved, the implant is capable of expanding for disc height restoration. To maintain an engagement spacer 100 and an insertion tool, a driving end (not shown) of the tool is inserted into tool engagement 188. To prevent separation of the tool and spacer 100, a tool connector 192 may be provided, extending from or formed within screw support 60. In the embodiment shown in FIG. 16, for example, tool connector 192 extends from a surface of screw support 60B, and is releasably grasped by a mating tool portion.

Portions of spacer 100 may be radiopaque or radiotransparent. To improve visibility under imaging, radiopaque elements 194 may be provided in predetermined locations within spacer 100. In the embodiment of FIG. 16, for example, elements 194 are positioned within at least one of endplate 102B, 104B.

Implant spacers 100 of the disclosure can be positioned anterioriorly and continuously expanded to provide axial balance and greater endplate contact area, and allow for superior sagittal correction, and are insertable into the body through a smaller window, decreasing the need for damage and trauma to body tissue. Spacers 100 of disclosure provide the benefits of an ALIF device, implantable through a familiar posterior approach, decreasing surgery time and associated blood loss, as well as eliminating the need for an access surgeon.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A spacer for positioning between adjacent vertebral bodies, the spacer comprising:
a frame having a longitudinal axis, and having at least one ramped surface;
a first endplate configured to engage a first bone of a joint, and having at least one ramped surface mateable with a first ramped surface of the frame, whereby when the first endplate is moved relative to the frame in a direction along the longitudinal axis, at least one end of the first endplate is moved in a direction away from the frame to open the spacer;
a second endplate configured to engage a second bone of the joint, and having at least one ramped surface mateable with a second ramped surface of the frame, whereby when the second endplate is moved relative to the frame in a direction along the longitudinal axis, the second endplate is moved in a direction away from the frame to increase a height of the spacer,
an actuating screw moveable with respect to the frame and operationally engaged to the first endplate and configured to cause movement of the first endplate along the longitudinal axis of the frame when the actuating screw is moved with respect to the frame,
a nut threadably engaged with the actuating screw, the nut rotatable with respect to the frame to move the actuating screw with respect to the frame,
wherein the first endplate comprises a pair of ear portions, wherein each of the ear portions comprises an aperture.

2. The spacer of claim 1, wherein the spacer is moveable from a collapsed position to an open position, wherein, in the open position, a distal end of the spacer has a height that is greater than a height of a proximal end of the spacer.

3. The spacer of claim 1, wherein the spacer is moveable from a collapsed position to an open position, wherein, in the open position, the spacer may have a lordotic angle up to 12°.

4. The spacer of claim 1, wherein a pivot pin may pass through each of the apertures to pivotally couple the first endplate to a link.

5. The spacer of claim 1, wherein the link comprises a body portion having endplate engaging projections at one end.

6. The spacer of claim 5, wherein a pivot pin passes through one of the endplate engaging projections to pivotally couple the link to the first endplate.

7. The spacer of claim 5, wherein the body portion of the link comprises a slot, wherein a pin extends through the slot and through a head portion of the actuating screw to couple the link and the actuating screw.

8. The spacer of claim 1, wherein the first endplate is curved along a substantial portion of its length.

9. The spacer of claim 1, wherein the nut comprises a circumferential groove, and a screw support at a proximal end of the frame comprises a circumferential groove, the spacer further comprising a ring configured to be positioned partially within both the groove in the nut and the groove in the support, to rotatably retain the nut in connection with the frame.

10. A spacer for positioning between adjacent vertebral bodies, the spacer comprising:
a frame having a longitudinal axis, and having at least one ramped surface;
a first endplate configured to engage a first bone of a joint, and having at least one ramped surface mateable with a first ramped surface of the frame, whereby when the first endplate is moved relative to the frame in a direction along the longitudinal axis, at least one end of the first endplate is moved in a direction away from the frame to open the spacer;

a link moveable with respect to the frame, the link having a projection pivotally engageable with the first endplate to thereby move the first endplate along the frame longitudinal axis when the link is moved with respect to the frame, an actuating screw moveable with respect to the frame and operationally engaged to the first endplate and configured to cause movement of the first endplate along the longitudinal axis of the frame when the actuating screw is moved with respect to the frame, a nut threadably engaged with the actuating screw, the nut rotatable with respect to the frame to move the actuating screw with respect to the frame.

11. The spacer of claim 10, where the spacer includes a second endplate configured to engage a second bone of the joint, and having at least one ramped surface mateable with a second ramped surface of the frame, whereby when the second endplate is moved relative to the frame in a direction along the longitudinal axis, the second endplate is moved in a direction away from the frame to increase a height of the spacer.

12. A spacer for positioning between adjacent vertebral bodies, the spacer comprising:

a frame having a longitudinal axis, and having at least one ramped surface;

a first endplate configured to engage a first bone of a joint, and having at least one ramped surface mateable with a first ramped surface of the frame, whereby when the first endplate is moved relative to the frame in a direction along the frame longitudinal axis, at least one end of the first endplate is moved in a direction away from the frame to open the spacer;

a second endplate configured to engage a second bone of the joint, and having at least one ramped surface mateable with a second ramped surface of the frame, whereby when the second endplate is moved relative to the frame in a direction along the frame longitudinal axis, the second endplate is moved in a direction away from the frame to increase a height of the spacer, a link moveable with respect to the frame, the link having a projection pivotally engageable with the first endplate to thereby move the first endplate along the frame longitudinal axis when the link is moved with respect to the frame;

an actuating screw moveable with respect to the frame and engaged to the link and configured to cause movement of the first endplate along the longitudinal axis of the frame when the actuating screw is moved with respect to the frame, a nut threadably engaged with the actuating screw, the nut rotatable with respect to the frame to move the actuating screw with respect to the frame.

* * * * *